United States Patent [19]
Tian et al.

[11] Patent Number: 5,671,353
[45] Date of Patent: Sep. 23, 1997

[54] METHOD FOR VALIDATING A DIGITAL IMAGING COMMUNICATION STANDARD MESSAGE

[75] Inventors: Helen He Tian, Plano, Tex.; Brian C. Madsen, Carpinteria, Calif.; Donald Mason, Garland, Tex.

[73] Assignee: Eastman Kodak Company, Rochester, N.Y.

[21] Appl. No.: 602,412

[22] Filed: Feb. 16, 1996

[51] Int. Cl.$^6$ ......................................... G06F 11/00
[52] U.S. Cl. .............................. 395/185.01; 395/183.13; 364/413.13
[58] Field of Search .................. 395/185.01, 185.02, 395/183.01, 183.21, 183.13; 364/413.13, 413.15, 413.19, 419.19, 419.18

[56] References Cited

U.S. PATENT DOCUMENTS

| | | | |
|---|---|---|---|
| 5,117,351 | 5/1992 | Miller | 395/650 |
| 5,119,444 | 6/1992 | Nishihara | 582/42 |
| 5,289,577 | 2/1994 | Gonzales | 395/163 |
| 5,469,353 | 11/1995 | Pinskey et al. | 364/413.01 |
| 5,513,101 | 4/1996 | Pinsky et al. | 364/401 |

OTHER PUBLICATIONS

Brinkley, "A Distributed, Object Oriented Framework for Medical Image Management and Analysis: Application to Evaluation of Medical Image Segmentation Technqiues", Biomedical Image Analysis, 1994 Workshop, IEEE, pp. 194–203 1994.

Kester et al., "Imfomed: A New Component in the Cadans Computer Network", Computer in Cardiology, IEEE, pp. 529–532 1995.

Claesen et al., "American Society for Echocardiography Software Suite for Verification and Playback of Ultrasonic Cline–Mode Images" Computers in Cardiology, IEEE, pp. 581–583 1995.

Kitney et al., "An Object Oriented Multi–Modality Display and Analysis System Incorporating DICOM3", Computers in Cardiology, IEEE, pp. 181–183 1994.

Digital Imaging and Communications in Medicine (DICOM); Part 1 and overview, NEMA Standards Publication PS3.1 (199x), pp. 1, 3, 5, 7, 9, 11, 13, and 15, final draft Mar. 27, 1992.

*Primary Examiner*—Robert W. Beausoliel, Jr.
*Assistant Examiner*—Joseph E. Palys
*Attorney, Agent, or Firm*—William F. Noval

[57] ABSTRACT

The present invention provides an object oriented structure existing on a digital computer or PACS and a method, executed on a digital computer or PACS. The invention comprises a structure providing a plurality of semantic definition and validation objects and a method which semantically validates a DICOM message by passing the message through the structure. DICOM messages are comprised of a plurality of elements. A plurality of these elements are grouped into a module. A plurality of modules are grouped into an Information Entity (IE). A plurality of IEs are grouped into an Information Object Description (IOD). A plurality of IODs are grouped into a block. A plurality of blocks comprise a DICOM message. The semantic validation objects provide a structure and method for defining, examining and semantically validating the Elements, Modules, IEs, IODs, and Blocks which comprise a DICOM message. The present invention generates warnings regarding the semantic validation of the DICOM message. These warnings are stored in the list created in computer memory by the application program requesting validation. The transformed physical image is stored into computer memory and transfered via a DICOM message after the application program has received a list of semantic warnings from the present invention.

20 Claims, 15 Drawing Sheets

METHOD FOR VALIDATING A DIGITAL IMAGING COMMUNICATION STANDARD MESSAGE

BACKGROUND OF THE INVENTION

1. Field of the Invention

The present invention relates generally to the field of digital medical imaging communications and in particular to a method for semantically validating digital messages in a digital imaging system which are formatted according to the Digital Imaging Communications in Medicine (DICOM) standard.

2. Background Technology

Modern hospitals utilize digital medical images derived from a variety of imagery source devices. These digital medical images are sent and received over computer networks to enable medical professionals to view and diagnose digital medical imagery at a convenient computer workstation. Hospital personnel commonly employ a Picture Archival and Communications System (PACS) to send and receive digital medical images to workstations. In order to facilitate communications of medical images and associated information, industry personnel have developed the Digital Imaging Communications in Medicine (DICOM) standard.

The DICOM standard provides a common format for messages sent and received between a PACS and a workstation or between two or more PACS. PACS users send digital medical imagery encapsulated within DICOM standard messages, which enable users to send and receive imagery between workstations and between PACS. Unfortunately, there is no provision in a typical PACS for checking or validating the semantics of DICOM messages to ensure that the messages actually conform to the DICOM standard. PACS users can easily generate DICOM messages that appear to be in conformance with the DICOM standard, but are in fact confusing or unintelligible when received by a recipient PACS. Thus, there is a need for a method and apparatus to semantically validate DICOM messages.

SUMMARY OF THE INVENTION

The present invention provides a method and apparatus to semantically validate DICOM messages to facilitate the transmission of digitized medical imagery in a PACS. A first application program residing in a PACS transforms a physical medical image, which typically comprises a sheet of exposed radiological film, into a digital representation or digital medical image. The digital image is stored in computer memory provided by the PACS. The digital image can then be transmitted to any other PACS or application or device associated with the PACS. A second application program creates a DICOM message which encapsulates the digital image. The second application program then send the digital image to a desired destination. A third application program receives the DICOM message containing the digital image. Prior to sending the DICOM message, the second application which creates the DICOM message places an empty validation list into memory and passes the list to the validation method of the present invention.

The present invention provides an object oriented structure existing on a digital computer or PACS and a method, executed on a digital computer or PACS. The invention comprises a structure providing a plurality of semantic definition and validation objects and a method which semantically validates a DICOM message by passing the message through the structure. DICOM messages are comprised of a plurality of elements. A plurality of these elements are grouped into a module. A plurality of modules are grouped into an Information Entity (IE). A plurality of IEs are grouped into an Information Object Description (IOD). A pluratility of IODs are grouped into a block. A plurality of blocks comprise a DICOM message. The semantic validation objects provide a structure and method for defining, examining and semantically validating the Elements, Modules, IEs, IODs, and Blocks which comprise a DICOM message.

The present invention generates warnings regarding the semantic validation of the DICOM message. These warnings are stored in the list created in computer memory by the application program requesting validation. The transformed physical image is stored into computer memory and transfered via a DICOM message after the application program has received a list of semantic warnings from the present invention.

The present invention transforms a physical image such as an image captured on radiological film into a digital representation, and validates a DICOM message containing the image using the structure of objects provided by the present invention. The structure of the present invention provides a dictionary or class of defining objects for each successive level of each DICOM message. The present invention provides a dictionary or defining class of obects for each Element, Module, IE, IOD and block of a DICOM message. The structure of the present invention also provides a set of rules and warnings for each level of a DICOM message. The application program creating a DICOM message creates a validation list in memory where it is transformed by the method of the present invention. The method of the present invention validates the DICOM message by accessing the structure provided by the present invention, By comparing the DICOM message to the definitions provided by the structure objects, the method of the present invention semantically validates the DICOM message and stores warnings in the application validation list existing in computer memory.

In one aspect of the present invention a method for validating a DICOM message is presented comprising the steps of transforming a piece of radiological film into a digital image; storing the digital image in computer memory; encapuslating the digital image in a DICOM message in computer memory; accessing a dictionary in computer memory to obtain a list of elements and modules comprising the DICOM message; building a validation list in computer memory for the DICOM message; accessing a dictionary in computer memory to obtain a set of rules for validating the elements and modules comprising the DICOM message; accessing a dictionary in computer memory to obtain a set of warnings associated with the rules for validating the elements and modules comprising the DICOM message; applying the rules to the elements and modules comprising the DICOM message; generating a warning when an element or module violates a rule; storing the warning in the validation list in computer memory so that an application which generated the DICOM message can examine the validation list to determine whether the DICOM message is semanticly usable.

In another aspect of the present invention an appartus for validating a DICOM message is presented comprising: a digital computer having a processor and computer memory; a dictionary class of objects stored in computer memory; an entry description class of objects derived from the dictionary class and stored in computer memory; an item description class of objects derived from the dictionary class and stored in computer memory; a module description class of objects derived from the dictionary class and stored in computer memory; an entry description class of objects derived from the dictionary class and stored in computer memory; an element description class of objects derived from the dictionary class and stored in computer memory; a semantic role description class of objects derived from the dictionary class and stored in computer memory; a semantic warning description class of objects derived from the dictionary class and stored in computer memory; and a semantic warning list stored in computer memory.

DETAILED DESCRIPTION OF A PREFERRED EMBODIMENT

Introduction

The structure and method of the present invention provide a validation sub-system for semantically validating incoming and outgoing DICOM messages, to ensure that the DICOM messages conform to the DICOM standard. In general, the entities which are validated comprise Composite Information Objects ((CIOs), query/retrieve identifiers, event (action) information, non-event information, command requests, response message lists, and real-world data and their corresponding decoded list of elements.

The present invention provides a structure of class dictionaries which enable the process of the present invention to determine the semantic requirements of each DICOM message under various operational conditions. Each class dictionary contains a series of pages or entries that contain definitions of the classes and messages. The structure provides at least one page or entry of the class dictionary for each class that exists. Class dictionary entries follow the same basic format providing the same basic information. Class information comprising the name of the file or object containing the class dictionary entry, the name of the class that the dictionary entry describes, a "subclassing value," which indicates whether subclassing performance is "never," "optional," or "required,"; the name of a parent class from which the class is derived, the name of the sub-subsystem to which the class belongs, the name of the author, a high-level definition of the class, a high-level list of attributes that belong to the class; a high-level list of responsibilities and collaborations of the class; and a list of elements, element values, modules, conditional rules or warnings.

Figure 1:
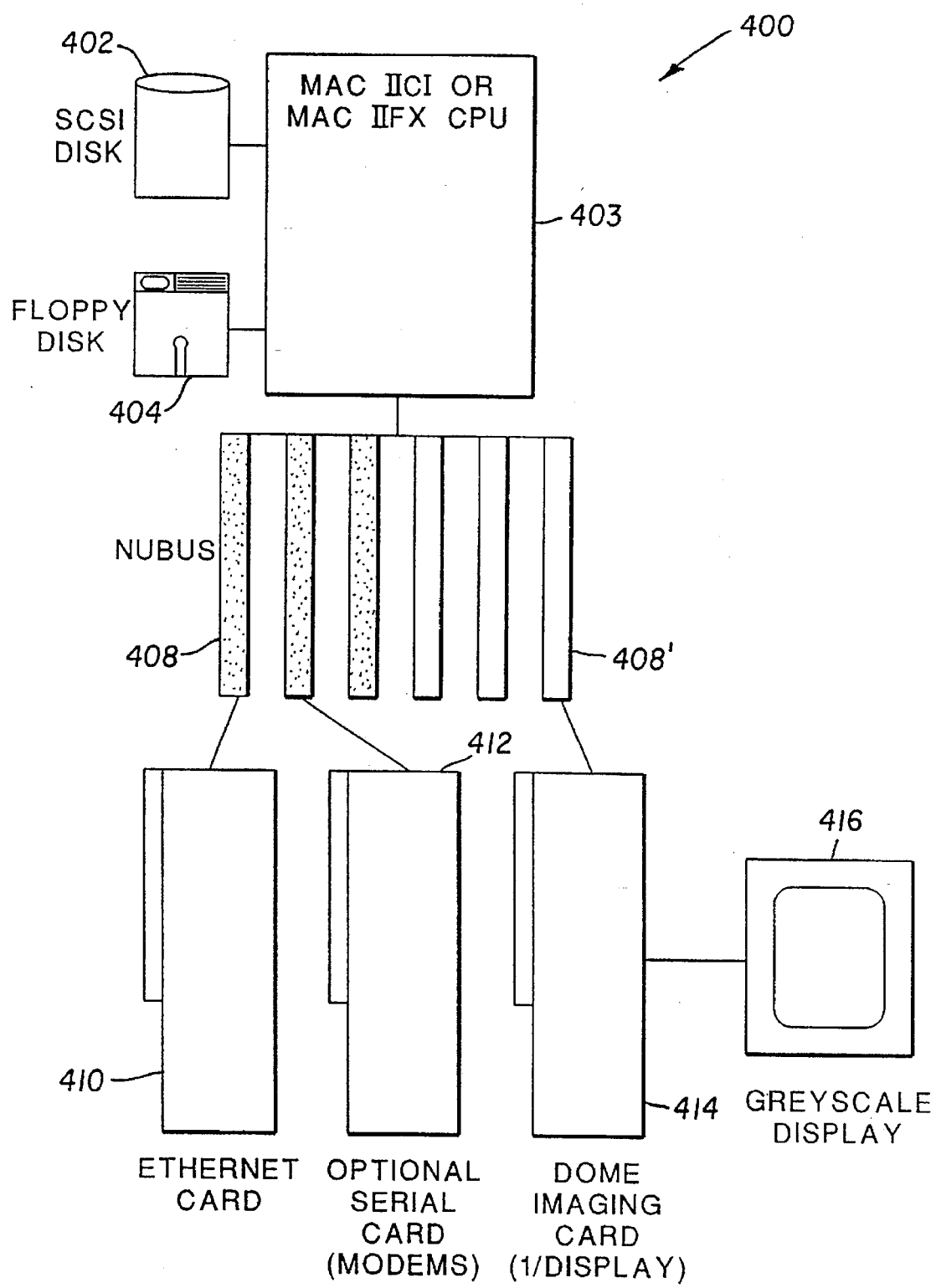
FIG. 1 is an illustration of a preferred embodiment the present invention embodied in a typical Picture Archival and Communications System.

Turning now to FIG. 1, in a preferred embodiment of the present invention, the structure of the present invention resides in a Picture Archival and Communications System (PACS). The PACS typically comprises a plurality of computers, computer memories, memory storage disks, read only memories, random access memories, and workstations for viewing and interaction with digital medical imagery. The structure provided by the present invention also provides a film digitizer which transforms physical medical imagery into a digital representation which is stored in computer memory residing in the PACS. The exemplary computer 400 shown in FIG. 1 includes CPU 402 (e.g., MAC II C1 or MAC II FX), SCSI hard drive 404, Floppy Disc 406, buses 408 (e.g., NUBUS), output cards 410 OETHERNET CARD), and 412 (MODEM), display driver card 414 (DOME IMAGING CARD), and gray scale display 416.

A user interacts with the digital medical imagery by entering commands at a workstation attached via a communications link to a local PACS. A user requests that a particular medical image be displayed at the workstation. Upon making the request, a first application existing in the local PACS creates a request to transfer the requested image from computer disk storage to the computer memory at the workstation. The medical image may exist, however, at a remote PACS location some physical distance from the local PACS and workstation. In this case, a second application existing at the remote PACS receives the image transfer request. The second application retrieves the requested image and creates a DICOM message containing the requested medical image which is then returned to the local PACS.

Due to the plurality of manufacturers or providers of PACS, a DICOM message created in a remote PACS may not be compatible with the local PACS. This is true, even though both the local PACS and the remote PACS are attempting to adhere to the DICOM standard. Thus, to ensure that the incoming DICOM message is actually compatible with the local PACS the present invention semantically validates the incoming DICOM message. The present invention also generates DICOM messages which are created by a local PACS to ensure adherance to the DICOM standard. The present invention generates a set of semantic warnings which indicate whether or not the DICOM message actually makes sense and is DICOM compatible. The application creating the DICOM message can then send the DICOM message or recreate it depending on the semantic warnings generated by the present invention.

DICOM requires certain elements or modules to be present under certain conditions. These elements and modules are referred to as conditional elements and modules. Conditional Modules are Mandatory Modules if specific conditions are met. If the specific conditions are not met, a warning is generated by the present invention.

DICOM also requires that elements have certain values, conditional values under certain conditions. DICOM requires that certain modules be present or absent under certain conditions. In the aggregate, these conditions total hundreds of not thousands of possible combinations and thousands of potential violations of the conditions, which can render a DICOM message meaningless or useless in terms of its utility in PACS operating under the DICOM standard.

The present invention provides object classes of rules and warnings, which do not exist in the DICOM standard. These rules and warnings semantically validate the thousands of possibilities using class rules, which are represented in a set of rule objects presented by the structure of the present invention. For example, a rules comprises: "element A must be present of element B is present"; or "element A must be present if element B is present and has a certain value"; and "element A must be present of element B exists and has a value within a specified range." The rules are represented in a rule language and reduced to a string test representing each rule. The structure of the present invention reduces the string test to a set of tokens which are stored in a data dictionary existing in computer memory. This token structure enables parsing each rule. Thus a DICOM message is reduced to an element list and processed according to the data dictionary rules for semantic validation. When the rules are violated, the method of the present invention generates a semantic warning and stores the warning in the semantic validation warning list created in computer memory by an application requesting validation.

Semantic warnings comprise statements like "required element missing." Thus an application is advised via a warning when a required element is missing from a DICOM message. Semantic warnings also comprise statements like "incorrect value," when, for example, an element has a list of appropriate enumerated values, but the value in the message is not one of the enumerated values.

The present invention also semantically validates DICOM messages regarding query and retrieval of medical imagery.

For example, when processing a query request to retrieve an image from an archive on computer memory disk storage, the present invention generates warnings regarding the semantic propriety of the query and retrieval request. The application sending a DICOM message also utilizes the present invention to determine whether or not the messages which it generates is DICOM compatible and semantically correct. The present invention also generates warnings regarding violations of rules such as "mutual exclusive information entities present" conflict warnings. The warnings are sufficiently similar so that they are all derived from the same parent object. Thus the warnings can be placed on a warning list in some descendent of the parent object.

Many of the terms that are used in this description of the invention are DICOM terms which are defined in the DICOM standard. The following symbols and abbreviations are used in this description and are defined in the DICOM standard, final draft Aug. 27, 1993, NEMA standards publication PS3.3 (199X). DICOM standard abbreviations and terms used in this description comprise the following:

ACR American College of Radiology

AE Application Entity

ANSI American National Standards Institute

DICOM Digital Imaging and Communications in Medicine

DIMSE DICOM Message Service Element

DIMSE-C DICOM Message Service Element-Composite

DIMSE-N DICOM Message Service Element-Normalized

IE Information Entity

IOD Information Object Definition

NEMA National Electrical Manufactures Association

OSI Open Systems Interconnection

SCP Service Class Provider

SCU Service Class User

SOP Service Object Pair

UID Unique Identifier

In a preferred embodiment of the present invention, an entity is used in an Entity-Relationship (E-R) model to represent a Real-World Object, class of Real-World Objects, or DICOM data representation, such as an IOD or Module. The DICOM Information Model defines the structure and organization of the information related to the communication of medical images. A Service Class Specification specifies related SOP classes which are defined as Service Groups, each of which comprise a group of DIMSE Service or Media Storage Service or Information Object Definitions which contain attributes.

An Information Object Definition (IOD) is an object-oriented abstract data model used to specify information about Real World Objects such as medical patients and their associated medical imagery. An IOD provides communication Application Entities with a common view of the information to be exchanged. An IOD does not represent a specific instance of a Real World Object, but rather a class of Real World Objects which share the same properties. An IOD which represents a single class of Real World Objects is referred to as a Normalized Information Object. When, in addition, an IOD includes information about related Real World Objects it is referred to as a Composite Information Object Definition (IOD).

A Composite IOD represents parts of several entities included in the DICOM Model of the Real-World. Such an IOD includes Attributes which are not inherent in the Real-World Object that the IOD represents but rather are inherent in the related Real-World Objects. These related Real World Objects provide a complete context for the exchanged information. When an instance of a Composite IOD is communicated, this entire context is exchanged between Application Entities. Relationships between Composite IOD Instances are conveyed in this contextual information or Composite IOD.

A Normalized IOD is an IOD which represents a single entity in the DICOM Application Model. Such an IOD includes Attributes which are only inherent in the Real-World Object that the IOD represents. Related Attributes are grouped into Modules which represent a higher level of semantics which are documented in the Module Specifications as defined in Annex C to part 3 of the DICOM standard. Attributes are encoded as Data Elements using Rule, Value Representation (VR) and the Value Multiplicity (VM) concepts as specified in Part 5 of the DICOM Standard. For specific Data Elements, the VR and VM are specified in a Data Dictionary found in Part 6 of the DICOM Standard.

For on-line communication, DIMSE Services enable a DICOM Application Entity to invoke an operation or notification across a network or point-to-point interface. DIMSE Services are defined in Part 7 of the DICOM Standard. For media storage interchange, Media Storage Services enable a DICOM Application Entity to invoke media storage related operations.

DIMSE-C Services are services applicable only to a Composite IOD. DIMSE-C Services provide only operation services. DIMSE-N Services are services applicable only to a Normalized IOD. DIMSE-N Services provide both operation and notification services. A DIMSE Service Group specifies one or more operations as defined in Part 7 of the DICOM Standard which are applicable to an IOD. DIMSE Service Groups are defined in Part 4 of the DICOM Standard, in the specification of a Service-Object Pair (SOP) Class.

A SOP Class is defined by the union of an IOD and a DIMSE Service Group. The SOP Class definition contains semantic rules which restrict the use of a service in the DIMSE Service Group and/or in the Attributes of the IOD. The selection of SOP Classes is used by Application Entities to establish an agreed set of capabilities to support their interaction. This negotiation is performed at association establishment time as described in Part 7 of the DICOM Standard. An extended negotiation enables Application Entities to further agree on specific options within a SOP Class. SOP Class operations and notifications comprise the methods of an object class.

The DICOM standard defines two types of SOP Classes, Normalized and Composite. Normalized SOP Classes are defined as the union of a Normalized IOD and a set of DIMSE-N Services. Composite SOP Classes are defined as the union of a Composite IOD and a set of DIMSE-C Services.

A Service Class Specification defines a group of one or more SOP Classes related to a specific function which is accomplished by communication Application Entities. A Service Class Specification also defines rules which enable implementations to state some pre-defined level of conformance to one or more SOP Classes. Applications may conform to SOP Classes as either a Service Class User (SCU) or Service Class Provider (SCP).

Each Composite IOD comprises an IOD Description, an IOD Entity-Relationship Model, and an IOD Module Table. An IOD Entity-Relationship Model provides the Entity-Relationship (ER) model which depicts the relationships of the components or Information Entities (IEs) of a specified IOD. An IOD ER forms an IOD specific Information Model. An ER model provides the complete context of how the image information is interpreted when an image is exchanged between two DICOM Application Entities.

Each image which is part of a specific study shares the same context, that is, all images within a specific patient study share the same patient and study information and all images within the same series share the same series information. A Patient ID defines the characteristics of a patient who is the subject of one or more medical studies which produce medical images. A Study IE defines the characteristics of a medical study performed on a patient. A study is a collection of one or more series of medical images, overlays and/or curves which are logically related for the purpose of diagnosing a patient. Each study is associated with exactly one patient.

A Series IE defines the Attributes which are used to group images; overlays and/or curves into distinct logical sets. Each series is associated with exactly one Study. An Equipment IE describes the particular imaging device which produced the series of images. An imaging device may produce one or more series within a study. The Equipment IE does not describe the data acquisition or image creation Attributes used to generate the images within a series. These Attributes are described in the Image IE.

An Image IE defines the Attributes which describes the pixel data of an image. Overlay, Lookup Table and Curve data may be included with in Image IE if this information is directly associated with the image.

An IOD Module Table defines the Modules comprising an IOD. The following information comprises the table: The name of the Module; a reference to a definition of the Module; and the usage of the Module (Mandatory, Conditional, or User Option). In a preferred embodiment, for each IOD, Mandatory Modules are supported per the definitions, semantics and requirements imposed on by a set of rules provided by the structure of objects of the present invention.

A Module Definition is composed of the following sections: A Module Description, a Module Definition, and an Attribute Description. The Module Definition enumerates each Attribute contained in the Module. For each Attribute the following information is provided: Attribute Name, Data Element Tag, Type Designation, and Attribute Definition. The Attribute Name is used to provide a reference to an Attribute. Each Attribute is provided with a unique Attribute Tag which serves as an index into a Data Dictionary. Each Attribute contained in a Module referenced by a Composite IOD defines a Type designation which indicates if a specific Attribute is required by all DIMSE operations/notifications associated with a SOP Class using the Module. The Type designation given in a Module is a default value and as such may be overridden by an IOD referencing the Module. A brief description is provided for each attribute in the Module definition table. The description provides a context for the use of the Attribute and provides general elucidation. Defined Terms and Enumerated Values applicable to the Attribute may also be listed in the Attribute Description.

In a preferred embodiment, the present invention provides a parent class, DTMessage, which is the parent class for DICOM DIMSE service messages. The purpose of this class and all of the derived classes is to encapsulate all of the attributes that are needed to compose a semantically valid DICOM message. Various aspects of dealing with these attribute lists are separated into the different levels of the DTMessage inheritance for the purpose of reuse.

DTSynItemEntryDescription provides an abstract class to describe an item that is part of a semantics module dictionary entry.

DTElementModuleDescription provides a semantic description of an element that is part of a module. DTModuleDictionaryEntry owns a list of DTElementModuleDescription objects, that describe the elements that are part of a particular module.

DTModuleIodDescription provides a description of a module that is part of a composite IOD. DTCompositeIodDictionaryEntry owns a list of DTModuleIodDescription objects that describe the modules that are part of a particular composite IOD.

DTElementSopDescription provides a semantic description of an element that is part of a Non-Event module or an event type of an event SOP.

DTKeyImLevelDescription provides a semantic description of a query key element that is part of an IM level.

DTElementRule provides a general description of an element requirement condition rule. This class understands all of the types of rule patterns provided by the present invention.

DTDictionaryEntry is an abstract class of items that are contained in a list by a DTDictionary class. This class identifies the name of a dictionary entry. It also points to a list of DTItemEntryDescription objects, which describe the items that are in this dictionary entry.

DTSemanticsModDictionaryEntry is an abstract class of items that are contained in a list by the DTSemanticsModDictionary class. This class identifies the name of a semantics module dictionary entry. It also points to a list of DTSynItemEntryDescription objects, which describes the items that are in this dictionary entry.

DTCompositeIodDicEntry is a class of items that are contained in a list by the CompositeIodDictionary object. This object identifies the name of a Composite IOD. It also points to a list of DTModuleIodDescription objects, which describe the modules that are in a particular composite IOD.

DTModuleDictionaryEntry provides a list of instances of a class which makes up the content of a single instance of DTModuleDictionary. This object identifies the name of a module and contains a list of pointers to DTElementModuleDescription objects, which describe the attributes used in a particular module.

DTNormalizedSopIodDicEntry is a class of items which are contained in a list by the DTNormalizedSopIodDictionary object. This object identifies the name of a normalized SOP IOD, for example, "Basic Film Session SOP Class." It also points to a DTEventModuleSopDescription object and a list of DTNonEventModuleSopDescription objects, which describe each DIMSE service related IOD subset definition associated with a normalized SOP IOD entry, for example, "Basic Film Session SOP class N-CREATE Attributes."

DTImDictionaryEntry is a class of items that are contained in a list by the ImDictionary object. This object identifies the name of an Information Module (IM). It also points to a list of FTLevelImDescription objects, which describe the levels that are in a particular IM.

DTEventModuleDicEntry is a class of items that are contained in a list by the EventModuleDictionary object. This object identifies the name of a normalized event SOP IOD module. It also points to a list of DTEventTypeEventDescription objects, which describe each element that is associated with a particular normalized SOP IOD module.

DTModuleDictionaryEntry is a class which holds a table for service request and service response message fields and status types defined in service protocol and annex C "status types encoding" in part 7, of the DICOM standard. This class identifies the name of a table and contains a list of pointers to DTElementModuleDescription objects, which describe the Attributes used in a particular module.

DTModuleDictionary is a dictionary for module and module-like entities, for example, command request message lists, command response message list as listed in part 7 of the DICOM standard. This enables looking up of a module entry, which in turn contains a list of elements, element requirements, and other information to be used in validation of data sets.

DTImDictionary is a dictionary for query/retrieve information models. The enable looking up an IM entry, which contains a list of IM levels to be used in IM validation.

DTGVInterface provides an interface to DT subsystems and enables an application user to access validation methods.

DTGVWarning provides a warning code and warning text which is returned to the application invoking validation. The warnings enable the application developer to identify and correct errors in a DICOM message of which the present invention generates validation warnings.

DTGVIoWarning is class subclass of class DTGVSemWarning. It represents Information Object related common warning information in validation. It provides access methods for an application to obtain an affected Information Object name.

DTGNVImWarning is a subclass of DTGVSemWarning. It represents an Information Model related common warning information in validation. It provides access methods for an application to obtain an affected Information Model name and query level.

DTGVUnpermittedWildcard is a subclass of DTGVImWarning. It represents warning information in validation regarding "Unpermitted_Wfidcard_Unique_Key_Or_Element." It provides access methods for an application to obtain an affected Information Model name, a wild card key or an element tag and warning string information. For a unique key, further information regarding a query level, wild card key level, affected SOP UID, and other information can be accessed. A user application is informed as to why the wild card is unpermitted.

DTGVUniqueKeyMissing is a subclass of DTGVImWarning. It represents warning information in validation related with a "Unique Key Missing." It provides access methods for a user application to obtain affected Information Model name, query level, missing key level, affected SOP UID, key tag, and other information from which a user application is informed as to which unique key is missing and why it is missing.

DTGVConditionalElemMissing is a subclass of DTGVIoWarning. It represents warning information in validation related to a conditional element missing. It provides access methods for an application user to obtain the affected SOP UID, missing element tag, IO name and other information to inform a user application as to which conditional element is missing and why it is missing.

DTGVMandatoryElemMissing is a subclass of DTGVIoWarning. It represents warning information in a validation related to a mandatory element missing. It provides access methods for a user application to obtain an affected SOP UID, missing element tag, IO name and other information to inform a user application as to which mandatory element is missing and why it is missing.

DTGVMutExcIEsPresent is a subclass of DTGVIoWarning. It represents warning information in validation related to more than one mutually exclusive IE being present. It provides access methods for an application user to obtain information regarding which SOP UID is affected, the IO name, a list of present mutually exclusive I.E.s to inform an application user as to which mutually exclusive I.E.s are present.

DTGVWarningSet is a wrapper class for DTGVRWSet to contain DTGBWarning objects provide by validation. An application using this class can access each of the warning objects in the set to determine which action to take or scan only those items of interest.

DTElementRule provides a general description of an element requirement condition rule. A subclass of this abstract class is derived for each rule pattern in a preferred embodiment.

DTElementInPattern provides a description of a specific rule type of element requirement condition. The pattern is as follows "Element X value matches pattern . . . specifically Element x value is in (Y11Y21 . . . Yn)."

DTElementNotExist provides a description of a specific rule type of element requirement condition. The pattern is as follows: "Element X does not exist."

DTElementInRange provides a description of a specific rule type of element requirement condition. The pattern is as follows: "Element x value is greater than Y1 and less than or equal to Y2."

DTElementHasValue provides a description of a specific role type of element requirement condition. The pattern is as follows: "Element X has value Y."

DTElementExist provides a description of a specific rule type of element requirement condition. The pattern is as follows: "Element X exists."

DTModuleReqConds reflects module conditions.

OPERATIONAL SCENARIOS

Figure 2:
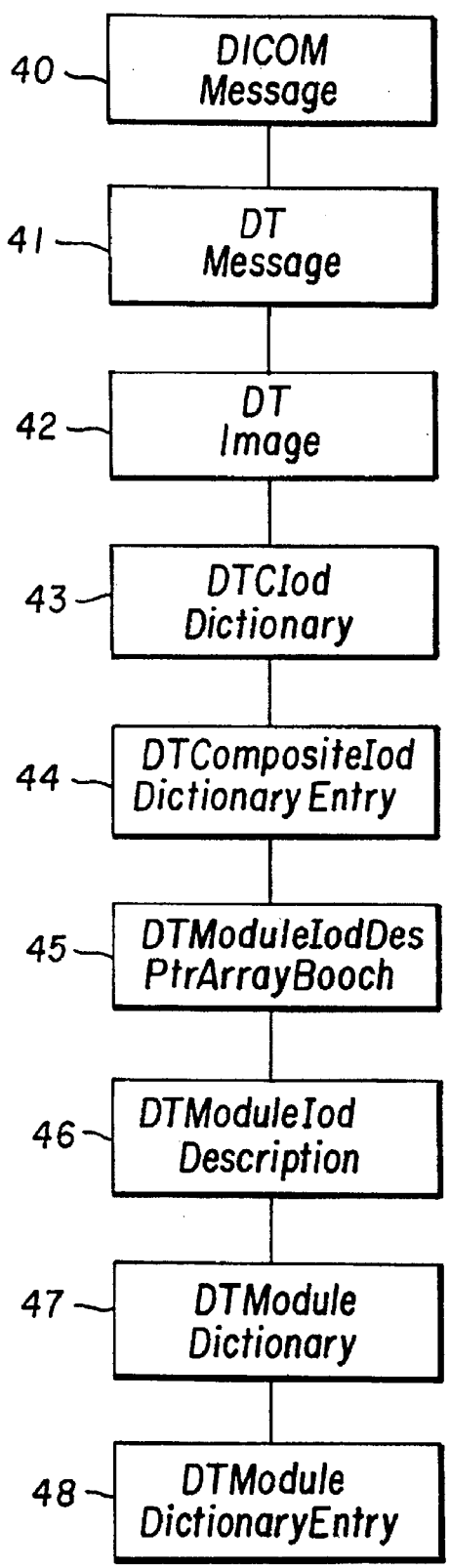
FIG. 2 illustrates a scenario in which a preferred embodiment of the process of the present invention semantically validates a Composite Information Object which does not contain a conditional module.

Turning now to FIG. 2, a scenario illustrating the validation method of a preferred embodiment is shown. In the scenario shown in FIG. 2, a Composite Information Object not having a conditional module is semantically validated. An application program receives or creates a DICOM message containing a composite IOD and accesses the dictionary DTMessage 41 to perform semantic validation of the DICOM message. DTMessage is the parent class for DICOM DIMSE service messages. The purpose of this class and all of the derived classes is to encapsulate all of the attributes that are needed to compose a valid DICOM message. Various aspects of dealing with these attribute lists have been separated into the different levels of the DTMessage inheritance for the purpose of reuse.

The validation process next obtains an Image Name and Element List for the composite IOD from DTImage 42 using methods getImageName and getElementList to obtain the Image Name and the Element List for the Composite IOD which is being validated. The process then obtains Entry Names for the Composite IOD from the dictionary DTCIodDictionary 43. DTCIodDictionary provides the dictionary for a Composite IOD. This dictionary enables lookup of a composite IOD dictionary entry which contains a list of modules comprising the composite IOD, module requirements, and other associated information used in the validation of data sets.

The process next obtains a list of module items from DTCompositeIodDictionary Entry 44. DTCIodDictionaryEntry 186 provides a class of items that are contained in a CompositeIodDictionary object This object identifies the name of a Composite IOD and points to a list of DTModuleIodDescription objects, which describe the modules that comprise the Composite IOD. The process then accesses DTCIodDictionaryEntry 186 which provides a class of items that are contained in a CompositeIodDictionary object This object identifies the name of Composite IOD and points to a list of DTModuleIodDescription objects, which describe the modules that are in this composite IOD. DTCompositeIodDictionary is a dictionary for the Composite IOD, which enables looking up or accessing of Composite IOD dictionary entries, which contain a list of modules, module requirements, and rules to be used in a validation of data sets.

The process next accesses DTModuleIodDesPtrArrayBooch 45 to obtain a pointer to validation information regarding Module Requirement types and Semantic Item Entry descriptions. The process then invokes methods getModuleReqType and validateSemItemEntryDes which access DTModuleIodDescription 46 to obtain module requirement types and a description of semantic item entries. DTModuleIodDescription provides a description of a module that is part of a Composite IOD. DTCompositeIodDictionaryEntry owns a list of DTModuleIodDescription objects that describe the modules that are part of a particular composite IOD. The process then accesses DTModuleDictionary 47 using the method getByEntryName. DTModuleDictionary is a dictionary for modules and module-like entities, for example, command request message lists and command response message lists. The method accesses a module entry in DTModuleDictionary to obtain a list of module elements, element requirements, and other information to be used in validation of data sets.

The process then accesses DTModuleDictonaryEntry 48 using method validateItems to validate the list of items contained in the module. The process then accesses warning objects owned by DTModuleDictionaryEntry to validate the items present in the DICOM message. Each validation is performed according to a set of rules which are associated with the entity being validated. Each rule set is kept in a data dictionary derived from a parent Rule object or dictionary. The process of the present invention compares the items to the rules and generates warnings which are stored in memory and sent to a user application to indicate semantic status after completing the validation process.

Figure 3:
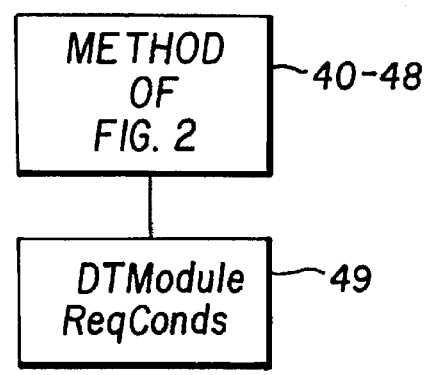
FIG. 3 illustrates a scenario in which a preferred embodiment of the process of the present invention semantically validates a Composite Information Object which contains a conditional module.

Turning now to FIG. 3, a scenario in which a Composite IOD containing a conditional module is depicted. This process steps executed in this scenario are similar to the steps executed in the scenario of FIG. 2, however, in the FIG. 3 scenario additional steps are performed to semantically validate the module requirement conditions for the conditional modules. In this conditional module scenario, the method getModuleRule is used to obtain Module Rules from DTModuleIodDescription after using method getModuleReqType to obtain Module Requirement Types from DTModuleIodDescription. The process then obtains module requirement conditions using the method matchRule to obtain the module requirement conditions from DTModuleReqConds 49. The scenario then proceeds as in the scenario depicted in FIG. 2, except that the module requirement and module rules are utilized to semantically validate the conditional modules present in the Composite IOD.

Figure 4:
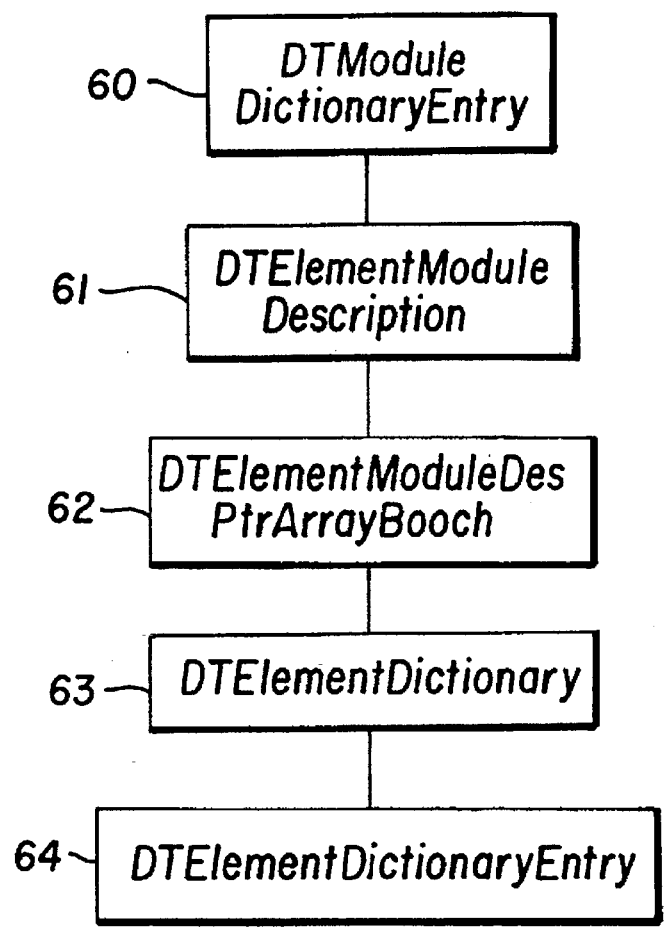
FIG. 4 illustrates a scenario in which a preferred embodiment of the process of the present invention semantically validates a Module which does not contain conditional elements.

Turning now to FIG. 4, a scenario is shown in which a module not having conditional elements is validated. The process of FIG. 4, as shown in this scenario starts by using method getAttributeList to access DTModuleDictionaryEntry 60 to obtain a list of attributes used in the module. DTModuleDictionaryEntry 60 provides a list of instances of a class which makes up the content of a single instance of DTModuleDictionary. DTModuleDictionaryEntry identifies the name of the module and provides a list of pointers to DTElementModuleDescription objects, which describe the attributes used in the module. The process then accesses DTElementModuleDesPtrArrayBooch 62 using the pointers obtained from DTModuleDictionaryEntry 60 to obtain the module elements from DTElementModuleDesPtrArrayBooch 62. The process then uses methods getElementReqType, validateElemSemantics, and validateElemSyntax to access DTElementModuleDescription 61. DTElementModuleDescription provides a semantic description of each element that is part of the module. DTModuleDictionaryEntry owns a list of DTElementModuleDescription objects that describe the elements that are part of the module. DTElementDictionaryEntry provides a list of instances of a single instance of the class DTElementDictionary. The process then uses method getEntryByTag to access DTElementDictionary 63 to obtain tags for the module elements. DTElementDictionary 63 provides access to tags which enable access to element VR, VM, and other information concerning the elements. The process then uses method validateSyntax to access DTElementDictionaryEntry 64 to validate the syntax of the module elements. Warnings are generated and sent to a user application to indicate semantic status after completing the validation process.

Figure 5:
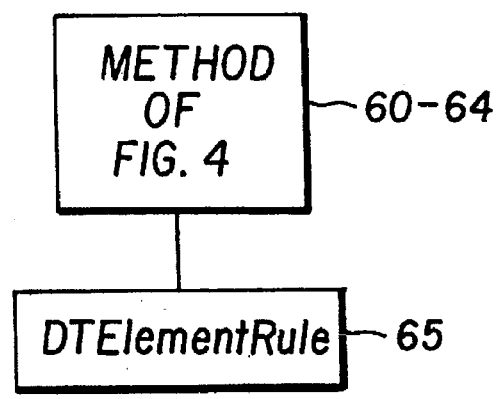
FIG. 5 illustrates a scenario in which a preferred embodiment of the process of the present invention semantically validates a Module which contains conditional elements.

Turning now to FIG. 5, a scenario in which the process validates a module containing conditional elements is depicted. The scenario of FIG. 5 is similar to the process steps taken in the scenario of FIG. 4, however, additional steps are taken to access semantic validation rules and generate semantic validation warnings. In the scenario of FIG. 5, after the methods getElementReqType and getElementRule access DTElementModuleDescription, the process then uses the method matchRule to access DTElementRule 55. DTElementRule provides a description of the applicable element requirement condition rules. All rule patterns are available in this object and are used to test semantic conditions associated with the elements. The process then proceeds as in the scenario of FIG. 4, except that semantics are also validated using the element rules. The process generates warnings which are written to memory when a element condition or rule is violated. The validation process access warning objects to test element conditions and to generate warnings.

Figure 6:
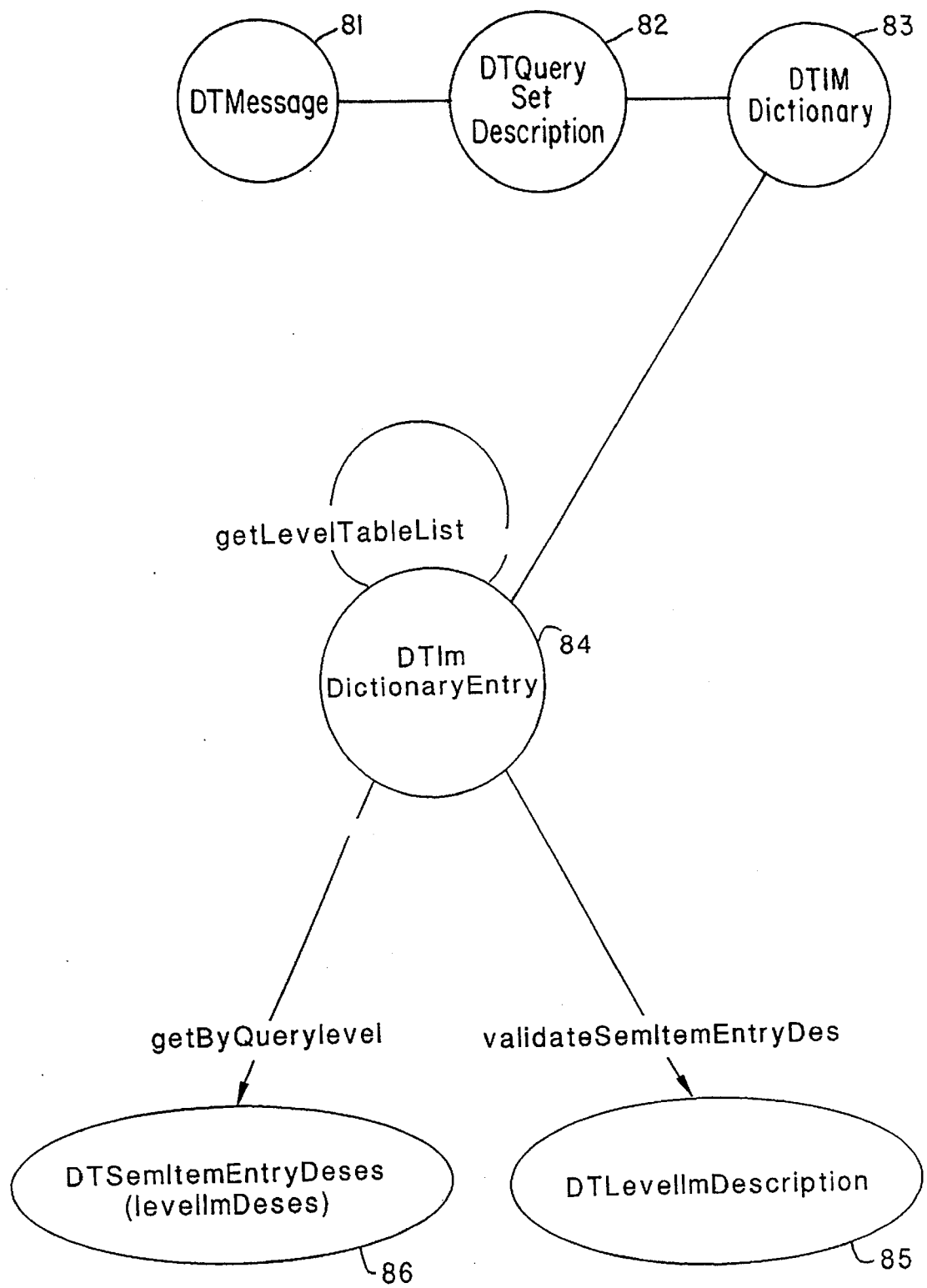
FIG. 6 illustrates a scenario in which a preferred embodiment of the process of the present invention semantically validates a Hierarchical Information Model Query Look Up or Access.

Turning now to FIG. 6 a scenario which validates a Hierarchical Information Model in a Query Level Look Up is depicted. In this scenario the first step is to access DTMessage 81. The next step of the process is to use the method validate to access DTQuerySetDescription 82. The process then uses methods getQueryLevel and getElementList to obtain the query level and the element list for the query. The next step in the process is to use the method getBySopUid to access DTImDictionary 83 to obtain the SOP UID for the query. The next step in the process is to use the method validateItems to access DTImDictionaryEntry 84. The process then uses the method getLevelTableList to obtain a list of levels from DTImDictionary 84 which is a class of items contained in a list by ImDictionaryObject. This object identifies the name of an Information Model (IM) and points to a list of FTLevelImDescription objects, which describe the level provided in the IM for the query. The process then uses the method getByQueryLevel to access the process DTLevelImDesPtrArrayBooch 85 to obtain a query level which appears on the list of FTLevelImDescription objects. The process then uses the method validateSemItemEntryDes to access DTIMLevelDescription 86. DTImLevelDescription provides a dictionary of levels for the IM, which enables access to an IM Level Entry, which contains a list of keys to be used in validation of a query/retrieve identifier. The process then accesses the rule and warning objects to validate the query level for the IM. Warnings are generated and sent to a user application to indicate semantic status after completing the validation process.

Figure 7:
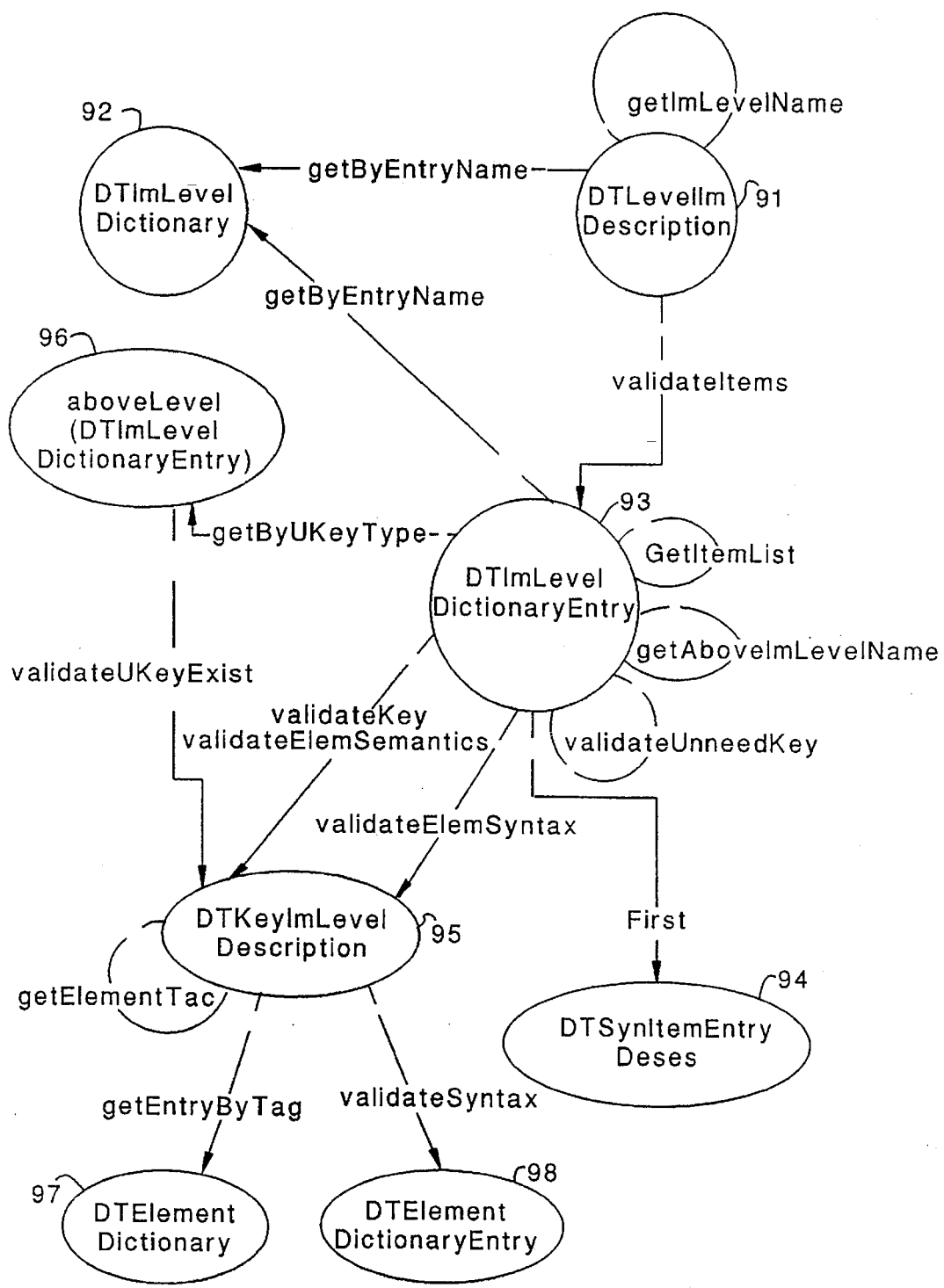
FIG. 7 illustrates a scenario in which a preferred embodiment of the process of the present invention semantically validates a Hierarchical Information Model Key.

Turning now to FIG. 7 a scenario depicting the process steps used in validation or a hierarchical Information Model in a keys checking scenario is presented. The first step in the process of the scenario shown is FIG. 7 is to access DTLevelImDescription using the method getImLevelName 91 to obtain an IM level name. DTLevelImDescription provides a description of a level that is part of the IM. The next step in the scenario is to use the method getByEntryName to access DTImLevelDictionary 92. DTImLevelDictionary provides a dictionary for the Levels of the IM. This enables access to an IM level entry, which contains a list of keys to be used in validation of query/retrieve identifiers. The next step in the scenario is to use the method validateItems to access DTImLevelDictionaryEntry. DTImLevelDictionaryEntry provides a class of items that are contained in a list by the ImLevelDictionary object. This object identifies the name of an IM level. It also points to a list of DTKeyImLevelDescription objects, which describe the keys that are in the IM Level. The process uses method getKeyList to obtain a list of keys for the IM from DTKeyImLevelDictionaryEntry. The next process step invokes the method First to access DTKeyImLevelDesPtrArrayBooch 94 to obtain a list of pointers to IM levels. The next step in the process is to use the method validateKey and validateElemSemantics to access DTKeyImLevelDescription 95. DTKeyImLevelDescription provides a semantic description of query key elements that are part of the IM Level. The next step in the process is to use the method getAboveImLevelName to access DTImLevelDictionaryEntry 93 to obtain an IM level name for the IM level which is above the current IM Level. The next step in the process is to access DTImLevelDictionary 92 using the method getByEntryName to obtain the entry name for the Level above the current Level. The next step of the process in the scenario of FIG. 7 is to access aboveLevel (DtImLevelDictionaryEntry) 96 using method getByUKeyType to obtain a key for the above Level. The process then accesses DTKeyImLevelDescription 95 using method validateUKeyExist to obtain a description of the Level. The next step in the process is to use the method validateUnneedKey to access DTImLevelDictionaryEntry to validate the Level Key. The next step is to use the method validateElemSyntax to access DTKeyKeyImLevelDescription to validate the syntax for Level Key.

The next process step is to use method getElementTag to obtain an element tag by accessing DTKeyImLevelDescription to obtain a tag for the Level. The next step in the scenario of FIG. 7 is to use the method getEntryByTag to obtain an element from DTElementDictionary using the tag for the element tag for the key. The next step in the scenario is to use the method validateSyntax to access the DTElementDictionaryEntry 98 to validate the key element syntactically. Warnings are generated and sent to a user application to indicate semantic status after completing the validation process.

Figure 8:
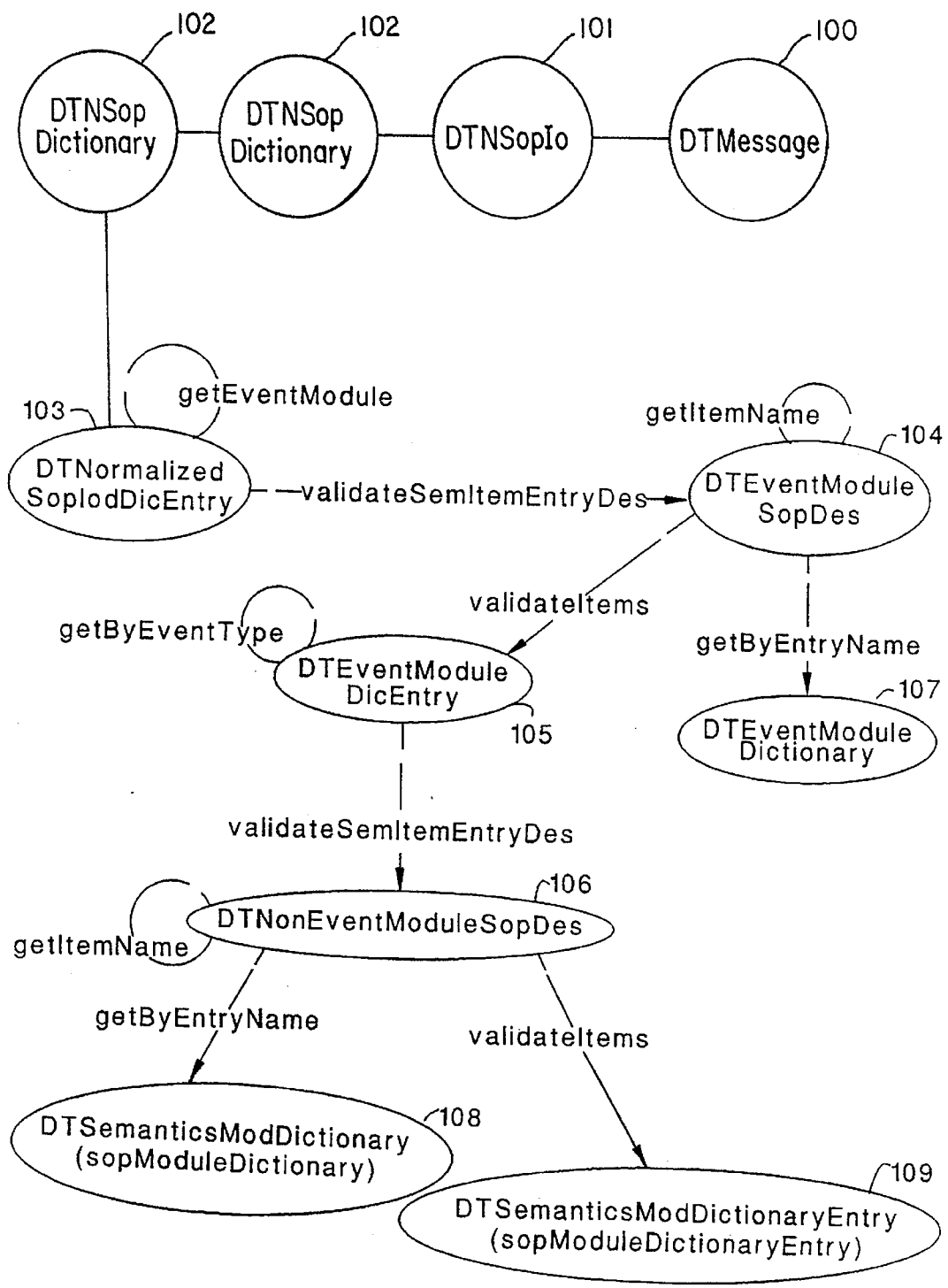
FIG. 8 illustrates a scenario in which a preferred embodiment of the process of the present invention semantically validates a Normalized Event SOP.

Turning now to FIG. 8 a scenario depicting the validation of a normalized event SOP is depicted. The first step in a process in executing this scenario is to access DTMessage 100. The next step in the process is to access DTNSopIo 101 using the validateSop method. The next step in the scenario is to access DTNSopIo 101 using method getScuSop to obtain the SCU and SCP for the normalized SOP. The next step is to access DTNSopDictionary 102 using the method getBySopUid to obtain the UID for SOP from DTNSopDictionary 102. DTNSopIodDictionary 102 is a dictionary for normalized SOPs. This dictionary enables access of a normalized SOP IOD dictionary entry, which comprises it list of event modules and non-event modules which are used in validation of the SOP, that is the modules which are semantically Valid in the SOP according to the semantic rules. The next step is to use the method validateItems to access DTNSopDictionaryEntry 103. DTNSopDictionaryEntry provides a class of items that are contained in a list by the DTNSopIodDictionary object. This object identifies the name of a normalized SOP IOD. It also points to a DTEventModuleSopDescription object and a list of DTNonEventModuleSopDescription objects, which describe each DIMSE service related IOD subset definition in the Normalized SOP IOD. The next step in the process is to access DTNSopDictionaryEntry using the method getEventModule to obtain an Event Module name. The next step in the scenario is to use the method validateSemItemEntryDes to access DTEventModuleSopDes 104. DTEventModuleSopDescription provides a description of an Event Module SOP that is part of the normalized SOP IOD. The next step is to use the method getItemName to access DTEventModuleSopDes 104 to obtain an item name. The next step in the process is to use the method getByEntryName to access DTEventModuleDictionary 107 to obtain an Entry Name. DTEventModuleDictionary provides a dictionary for normalized Event SOP IOD modules, which enables access of a normalized Event SOP IOD module dictionary entry, which comprises a list of event types which are used in the validation of data sets. The next step in the process is to use the method validateItems to access DTEventModuleDictEntry 105. DTEventModuleDictEntry provides a class of items that are contained in a list by the EventModuleDictionary objects, which identifies the name of a normalized event SOP IOD module. It also points to a list of DTEventTypeDescription objects, which describe each element associated with a particular normalized SOP IOD module. Then next step in the process is to use the method getByEventType to access DTEventModuleDictEntry 105 to obtain an description by event type.

DTEventModuleDicEntry provides a class of items which are contained in a list by the EventModuleDictionary object, which identifies the name of a normalized event SOP IOD module. It also provides pointers to a list of DTEventTypeEventDescription objects, which describe each element that is associated with a particular normalized SOP IOD module. The next step in the process is to use the method validateSemItemEntryDes to access DTEventTypeEventDes 106 to validate the semantics of the Item Entry against the Description of the Item Entry. The next step in the process is use the method getItemName to access DTEventTypeEventDes 106 to obtain the name of the Item. DTEventTypeEventDescription provides a description of an Event Type that is part of an event. The next step in the process is to use the method getByEntryName to access DTSopModuleDictionary 107. DTSopModuleDictionary 107 provides a dictionary for a SOP module which contains both SCU and SCP related element information, which enables access of an SOP module dictionary entry. The entry comprises a list of DTElementSopDescription objects which are used in the validation of SOP items and elements. The next step in the process is to use the method validateItems to access DTSopModuleDictEntry 108. DTSopModuleDictEntry 109 provides a class of items that are contained in a list by the DTSopModuleDictionary object This object identifies the name of the SOP module. It also contains pointers to a list of DTElementSopDescription objects, which describe element that are in the dictionary entry. The validation process accesses associated semantic validation rules and methods to compare the items and elements against the items and element contained in the dictionary. The process generates warnings which are stored in memory and sent to a user application to indicate semantic status after completing the validation process.

Figure 9:
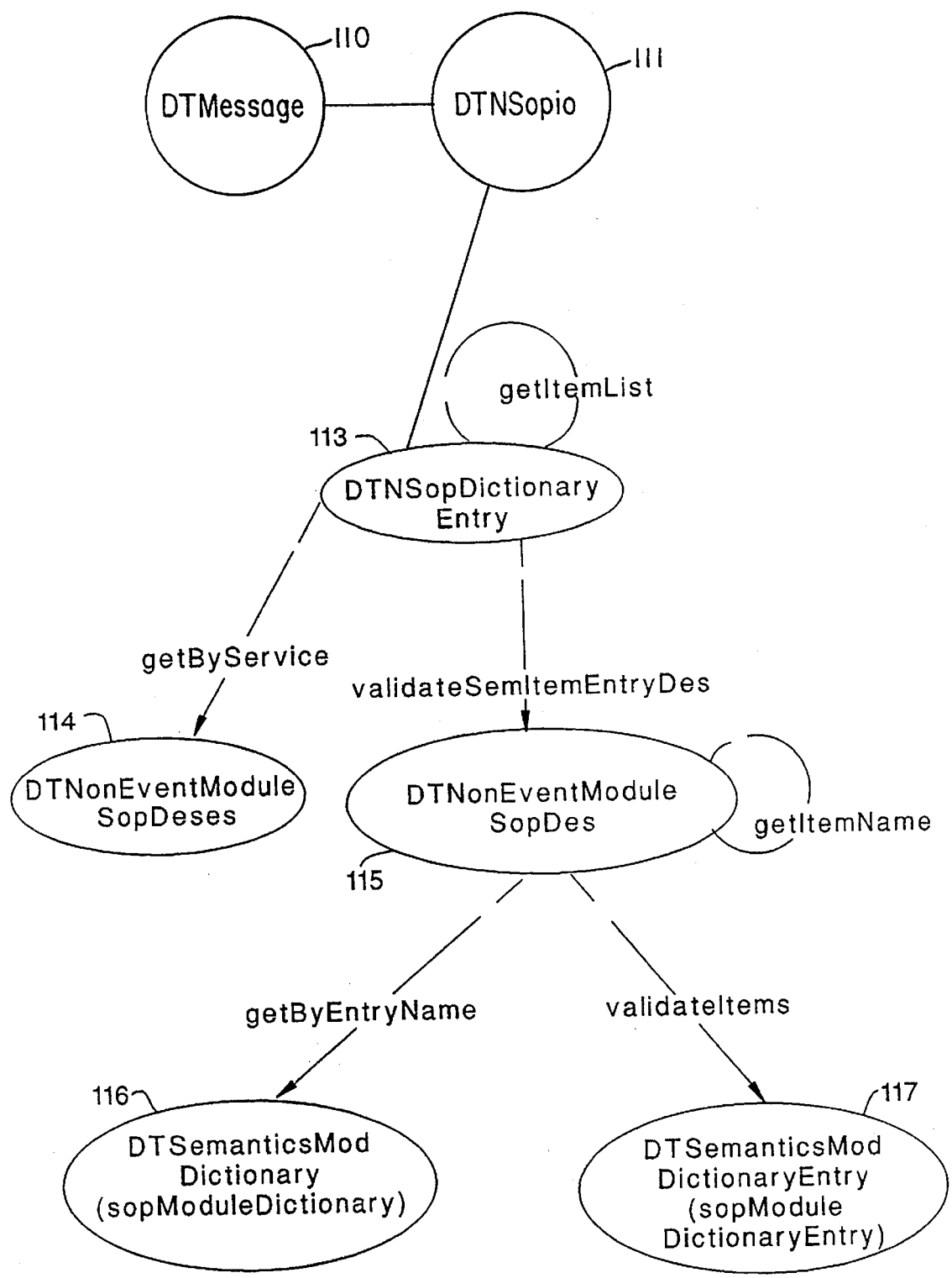
FIG. 9 illustrates a scenario in which a preferred embodiment of the process of the present invention semantically validates a Normalized Non-Event SOP.

Turning now to FIG. 9 a scenario in which the process of the present invention validates a normalized non-event SOP scenario is depicted. The process starts with an access to DTMessage 110. The process then uses method validateSop to access DTNSopIo 111. DTNSopIo comprises a dictionary for a normalized SOP IOD dictionary entry, which contains a list of event module and non-event modules which are used in the validation of the Normalized SOP. The process then uses method getItemlist to access DTNSopDictionaryEntry 113 which provides a class of items which are contained in a list by the DTNormalizedSopIodDictionary object This object identifies the name of a normalized SOP IOD, for example, "Basic Film Session SOP Class." The object also provides a pointer to a DTEventModuleSopDescription object and a list of DTNonEventModuleSopDescription objects, which describe each DIMSE service related IOD subset definition associated with the normalized SOP IOD entry, for example, "Basic Film Session SOP class N-Create Attributes." The process then uses the method getByService to access DTNonEventModuleSopDesArrayBooch 114 and obtain items for the SOP. The process then uses method validateSemItemEntryDes to access DTNonEventModuleSopDes 115. DTNonEventModuleSopDes provides a description of a Non Event Module that is part of a normalized SOP IOD. The process then uses the method getItemName to access DTNonEventModuleSopDes 115 to obtain item names for the SOP. The process then uses getByEntryName to access DTSopModuleDictionary 116 to obtain entries for the SOP entry names. The process then uses method validateItems to access DTSopModuleDictEntry 117. DTSopModuleDictEntry 116 provides a dictionary of the SOP module which contains both SCU and SCP related element information, which enables access to an SOP module dictionary entry. The entry containing a list of DTElementSopDescription objects which are used to validate the SOP elements. The process then accesses associated rules for semantic validation of the elements. The process uses the rules to semantically validate the elements and generates warnings which are stored in memory and sent to a user application to indicate semantic status after completing the validation process.

Figure 10:
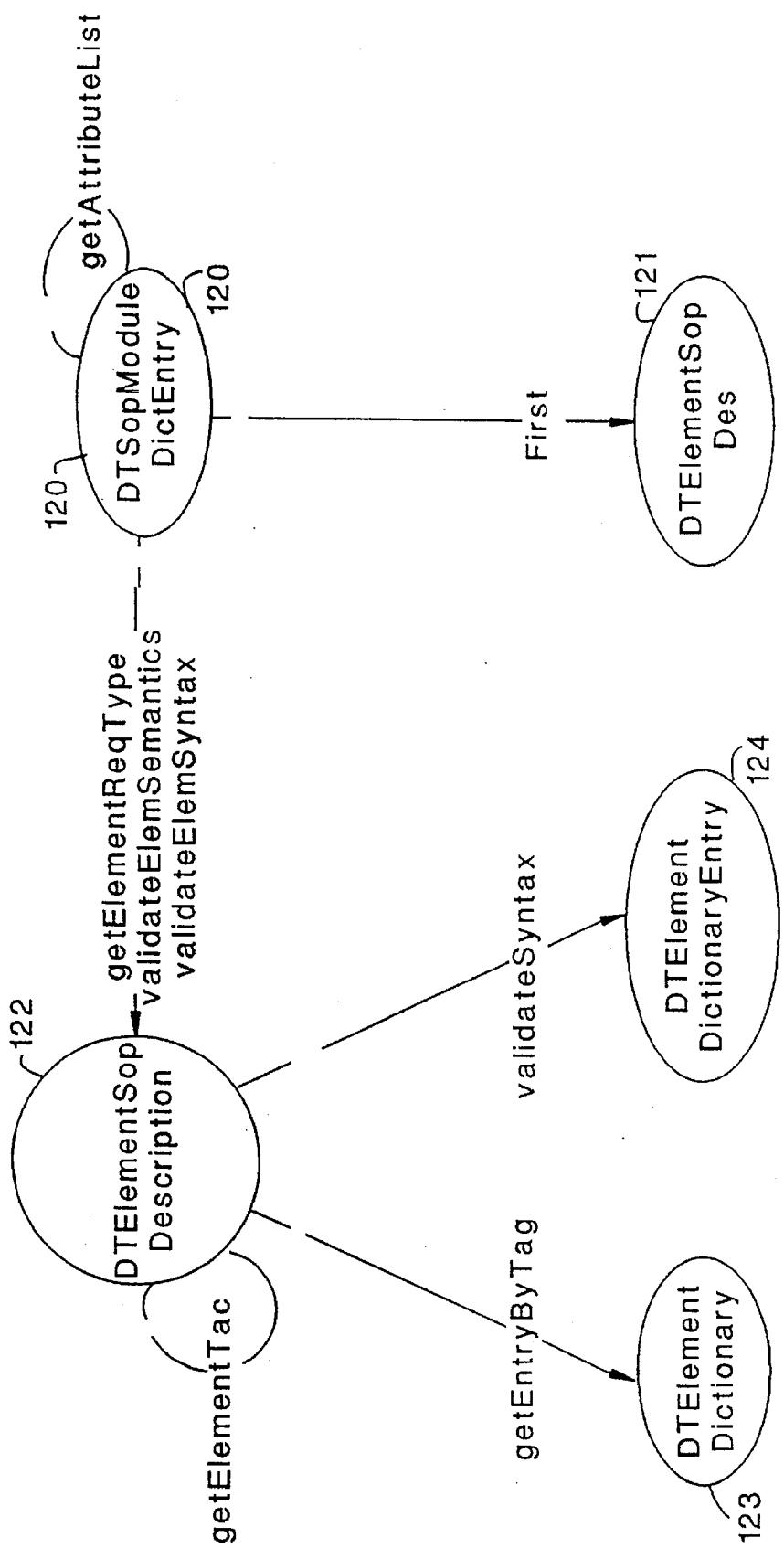
FIG. 10 illustrates a scenario in which a preferred embodiment of the process of the present invention semantically validates a SOP Module without conditional elements.

Turning now to FIG. 10, a scenario in which a SOP Module without conditional elements is validated. The first step performed by the process in the scenario of FIG. 10 is to obtain an attribute list from DTSopModuleDicEntry 120 using method getAttributeList. DTSopModuleDictEntry 120 provides a dictionary of the SOP module which contains both SCU and SCP related element information, which enables access to IO an SOP module dictionary entry. The entry contains a list of DTElementSopDescription objects which are used to validate the SOP elements. The process then uses method First to access DTElementSopDesArrayBooch 121 to obtain a list of elements for the SOP. The next step in the process is to obtain element requirement types from DTElementSopDescription using the method getElementReqType. The next step is to access DTElementSopDescription using validateElemSemantics and validateElemSyntax. The next step is to obtain element tags from DTElementSopDescription using the method getElementTag and to initiate validation of the elements semantically using method validateElemSemantics. The next step is to obtain element tags from DTElementSopDescription using the method getElementTag. The next step in the process is to obtain entries from DTElementDictionary 123 using the element tags. The next step in the process of the FIG. 10 scenario is to validate the elements syntactically using the method validateSyntax to access DTElementDictionaryEntry 124. The process accesses element rules and warnings to compare the elements to the rules and to generate warnings, which it stores in memory and are sent to a user application in a list to indicate semantic status after completing the validation process.

Figure 11:
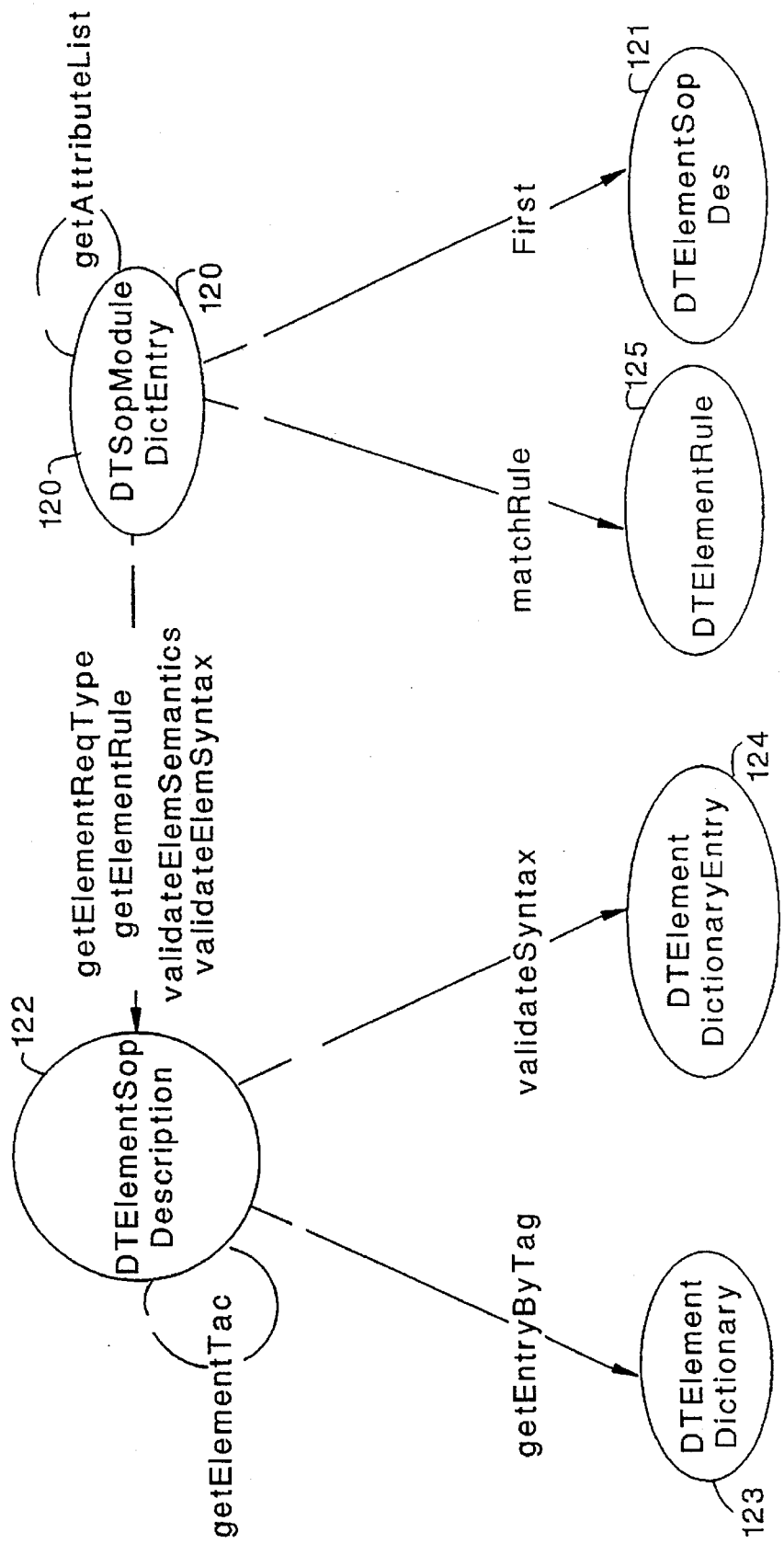
FIG. 11 illustrates a scenario in which a preferred embodiment of the process of the present invention semantically validates a SOP Module with conditional elements.

Turning now to FIG. 11, a scenario in which a SOP Module without conditional elements is validated. The first step performed by the process in the scenario of FIG. 11 is to obtain an attribute list from DTSopModuleDicEntry 120 using method getAttributeList. DTSopModuleDictEntry 120 provides a dictionary of the SOP module which contains both SCU and SCP related element information, which enables access to an SOP module dictionary entry. The entry contains a list of DTElementSopDescription objects which are used to validate the SOP elements. The process then uses method First to access DTElementSopDesArrayBooch 121 to obtain a list of elements for the SOP. The next step in the process is to obtain element requirement types and element rules from DTElementSopDescription using the method getElementReqType and getElementRule. The next step in the process is to access DTElementRule using the method matchRule to obtain the semantic validation rules for the elements. The next step is to access DTElementSopDescription using validateElemSemantics and validateElemSyntax. The next step is to obtain element tags from DTElementSopDescription using the method getElementTag and to initiate validation of the elements semantically using method validateElemSemantics. The next step in the process is to obtain entries from DTElementDictionary 123 using the element tags. The next step in the process of the FIG. 11 scenario is to validate the elements syntactically using the method validateSyntax to access DTElementDictionaryEntry 124. The process accesses element rules and warnings to compare the elements to the rules and generate semantic warnings which are stored in memory and sent to a user application to indicate semantic status after completing the validation process.

Figure 12:
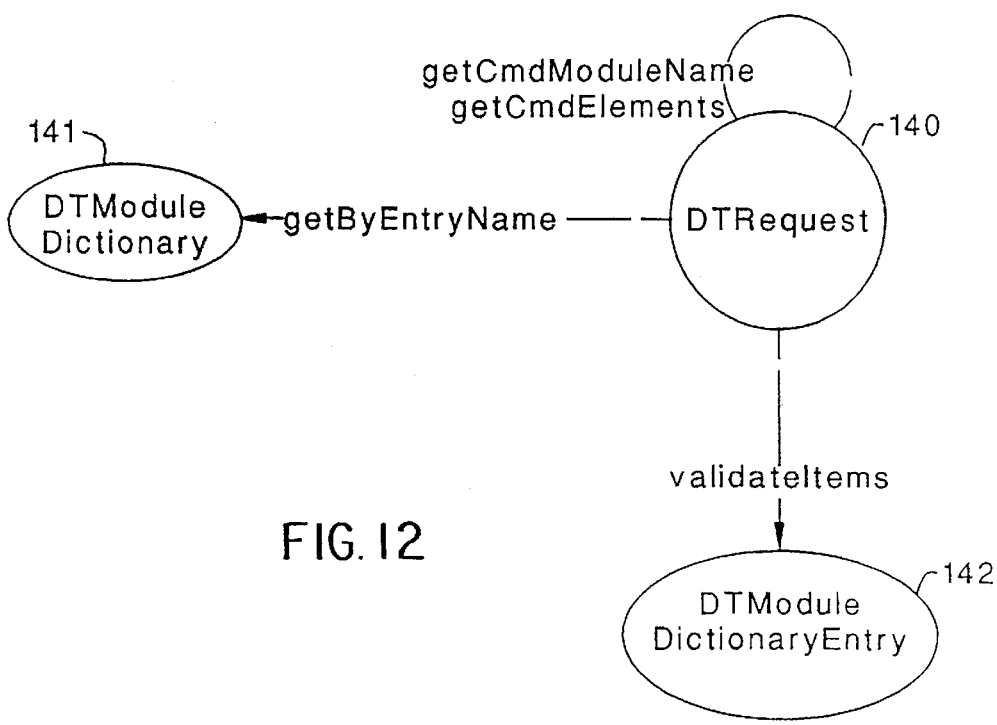
FIG. 12 illustrates a scenario in which a preferred embodiment of the process of the present invention semantically validates a DICOM command message.

Turning now to FIG. 12, a scenario is depicted in which a command is semantically validated. The first step in performing the scenario of FIG. 12 is to access DTRequest 140 using methods getCmdModuleName and getCmdElements to obtain the, command module names and command element names from the DTRequest dictionary which contains a list of modules names and elements for the command. The next step is to obtain the command entries using the method getByEntryName using entry names to access DTModuleDictionary 141. DTModuleDictionary provides a dictionary for module and module-like entities, for example, command request message list, and command response message lists. This dictionary enables access of a module entry, which in turn contains a list of elements, element requirements, and other information used in the validation of a command. The next step is to use validateItems to access DTModuleDictionaryEntry 142. DTModuleDictionaryEntry provides a class which holds a table for a service request and service response message fields and status types. The class identifies the name of a table, which in turn contains a list of elements, element requirements, and other information used in the validation of elements. The process accesses rules and warning objects to compare the elements to the rules and generates warnings which are stored in memory and sent to a user application to indicate semantic status of the command and its elements after completing the validation process.

Figure 13:
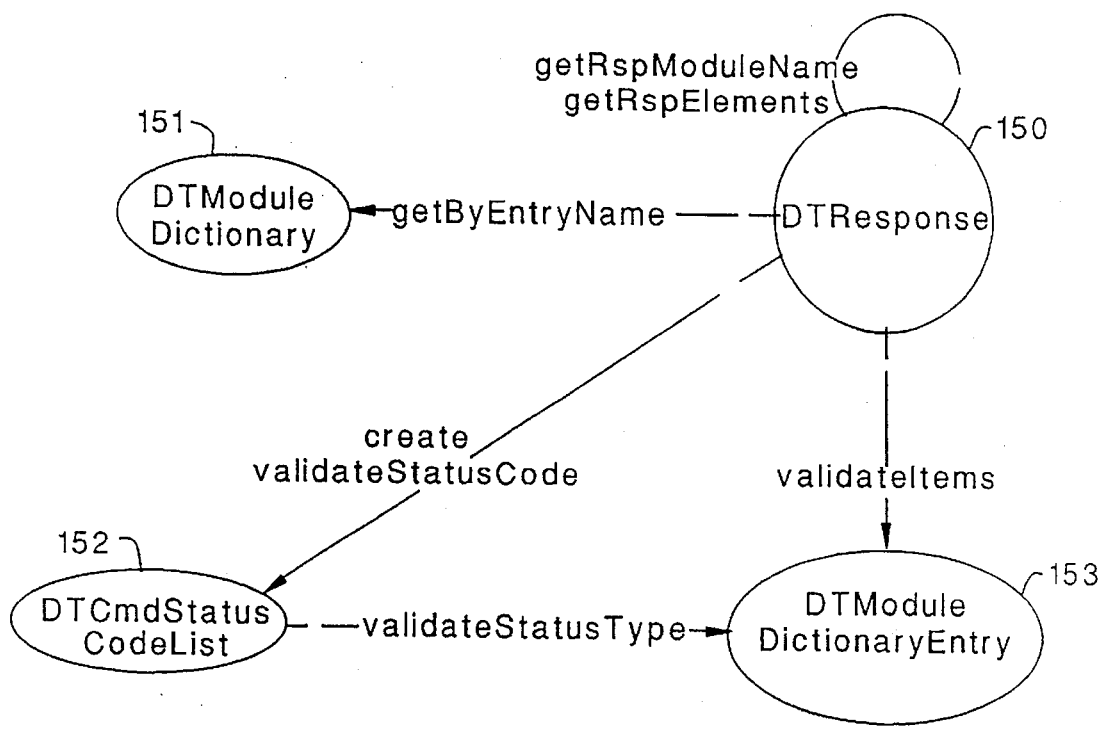
FIG. 13 illustrates a scenario in which a preferred embodiment of the process of the present invention semantically validates a DICOM response message.

Turning now to FIG. 13, a scenario in which a command response is semantically validated is depicted. The first step in the process in performing the scenario of FIG. 13 is to access DTResponse 150 to obtain a response module name and response elements names. DTResponse provides a class of Response module names and element names for the response. The next step is to obtain entries for the Response from DTModuleDictionary 15 1 using method getByEntryName using the response module names and element names. The next step in the process is to create a validation status code by accessing DTCmdStatusCodeList 152 which provides a list of command status codes for the response. The next step is to validate the status type using method validateStatusType to access DTModuleDictionaryEntry 153. DTModuleDictionaryEntry provides a list of instances of a class which makes up the content of a single instance of DTModuleDictionary. This object identifies the name of a module and contains a list of pointers to DTElementModuleDescription objects, which describe the attributes and elements of a particular module. The next step is to validate items in the command response using DTModuleDictonaryEntry 153. The process compares the response elements to the description of the elements and generates warnings which are stored in memory and sent to a user application in a list to indicate semantic status after completing the validation process.

Figure 14:
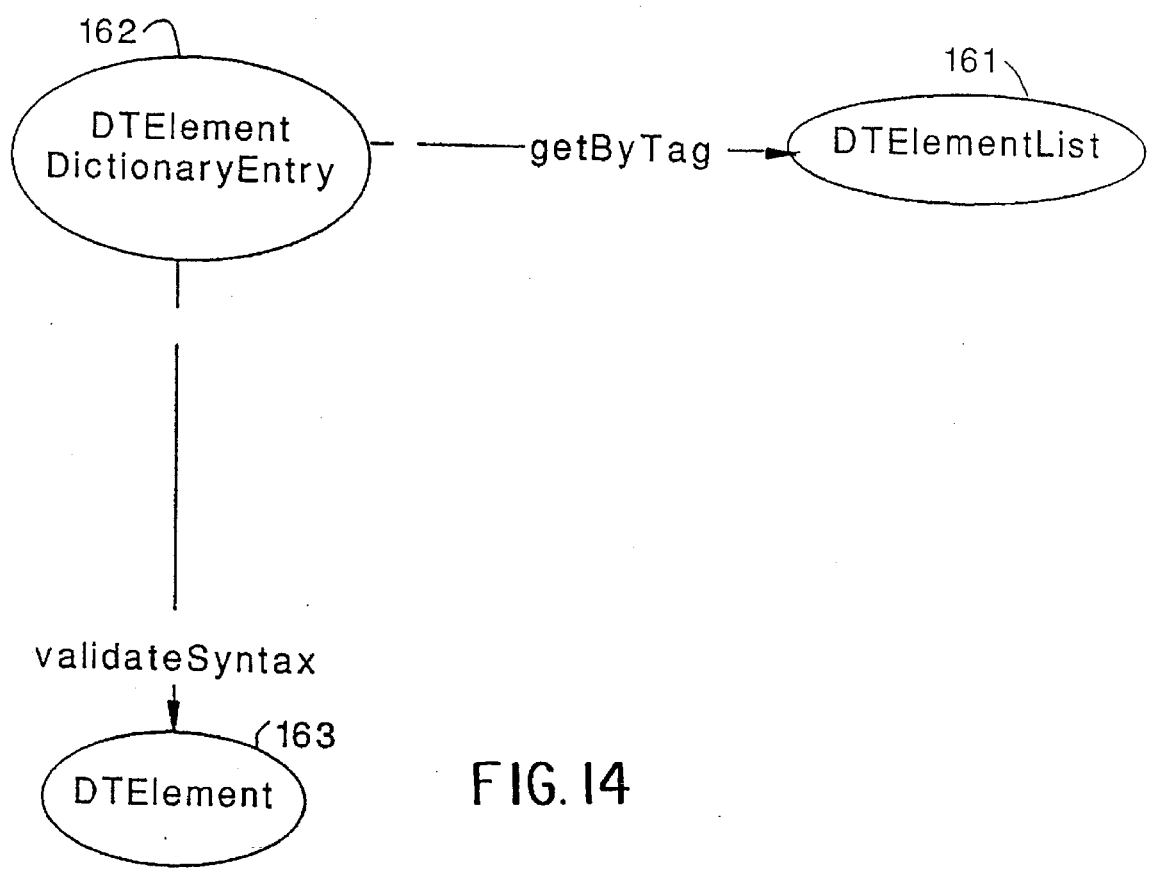
FIG. 14 illustrates a scenario in which a preferred embodiment of the process of the present invention validates an element syntax.

Turning now to FIG. 14, a scenario in which an element syntax is validated is depicted. In this scenario, the first step performed is to obtain an element list by tag name by accessing DTElementList 161. The next step is validate the syntax by accessing DTElement 163 which contains a description of element syntax. The process then generates warnings which are stored in memory, and sent to a user application in a list to indicate semantic status after completing the validation process.

Figure 15:
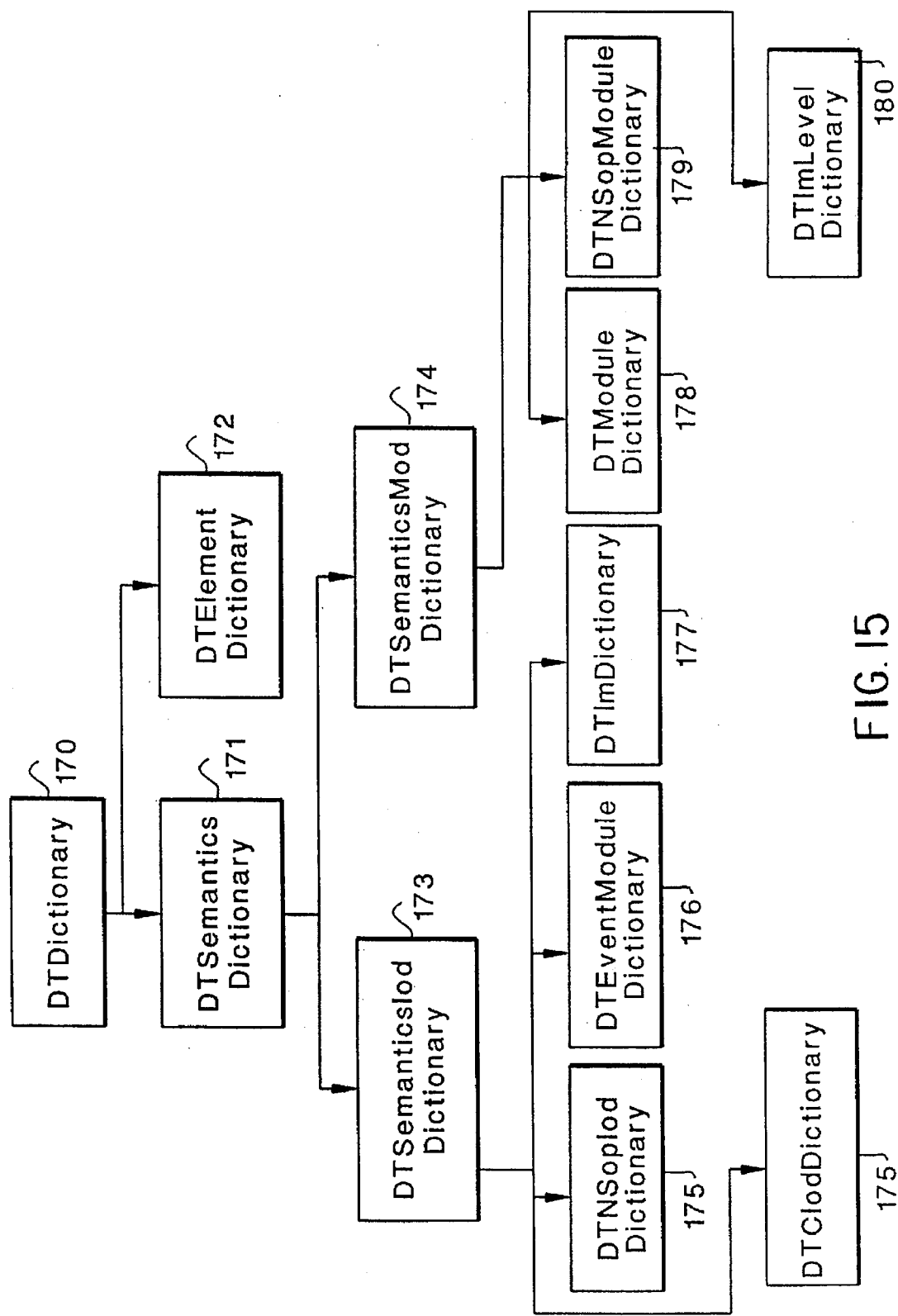
FIG. 15 is an illustration showing preferred inheritance relationships for DTDictionary in a preferred embodiment.

FIGS. 15–18 illustrate the inheritance and structure of objects provided by the present invention. Turning now to FIG. 15, the abstract class DTDictionary 170 is the parent class from which all dictionaries shown in FIG. 15 are derived. DTDictionary is an abstract Dictionary class which enables subclassing to various levels of dictionaries. It contains a Dictionary entry list which enables access to a specific Dictionary entry. DTSemanticsDictionary 171 provides an abstract class of semantics dictionary. This enables look up of a semantics dictionary entry, which in turn contains a list of DTItemEntryDescription objects to be used in validation of data sets. DTSemanticsIodDictionary 173 provides an abstract class of a semantics IOD dictionary. The enables lookup or access of a semantics IOD dictionary entry, which in turn contains a list of DTSemItemEntryDescription objects to be used in validation of data sets.

DTCIodDictionary 175 provides a dictionary for a Composite IOD. This dictionary enables lookup of a Composite IOD dictionary entry, which in turn contains a list of modules, module requirements, and other associated information used in the validation of data sets. DTNSopIodDictionary 195 provides a dictionary for SOP IODs. This dictionary enables lookup of a normalized SOP IOD dictionary entry, which in turn contains a list of event module and non-event modules to be used in validation of data sets. DTEventModuleDictionary 176 provides a dictionary for normalized event SOP IOD modules. This dictionary enables access of a normalized event SOP IOD module dictionary entry, which in turn contains a list of event types to be used in validation of SOP IODs. DTImDictionary 177 provides a dictionary for query/retrieve Information Models. This dictionary enables look up of an Information Model entry, which contains a list of keys to be used in key validation of an IM.

DTSemanticsModDictionary 174 provides an abstract class of a semantics module dictionary. This enables access of a semantics module dictionary entry, which in turn contains a list of DTSynItemEntryDescription objects to be used in validation of a module. DTModuleDictionary 178 provides a dictionary for modules and module-like entities such as command request message lists and command response message lists. This dictionary enables access of a module entry, which in turn contains a list of elements, element requirements and other information to be used the validation of module and its elements. DTSopModuleDictionary 179 provides a dictionary for an SOP module which contains both SCU and SCP related element information. This enables access of an SOP module dictionary entry, which in mm contains a list of DTElementSopDescription objects to be used to validate elements. DTImLevelDictionary 180 provides a dictionary for levels in a particular IM. This enables access of an IM level entry which in turn contains a list of keys to be used in validation of query/retrieve identifiers. DTElementDictionary 172 provides a dictionary which enables access of tags to find VR, VM, and other information.

Figure 16:
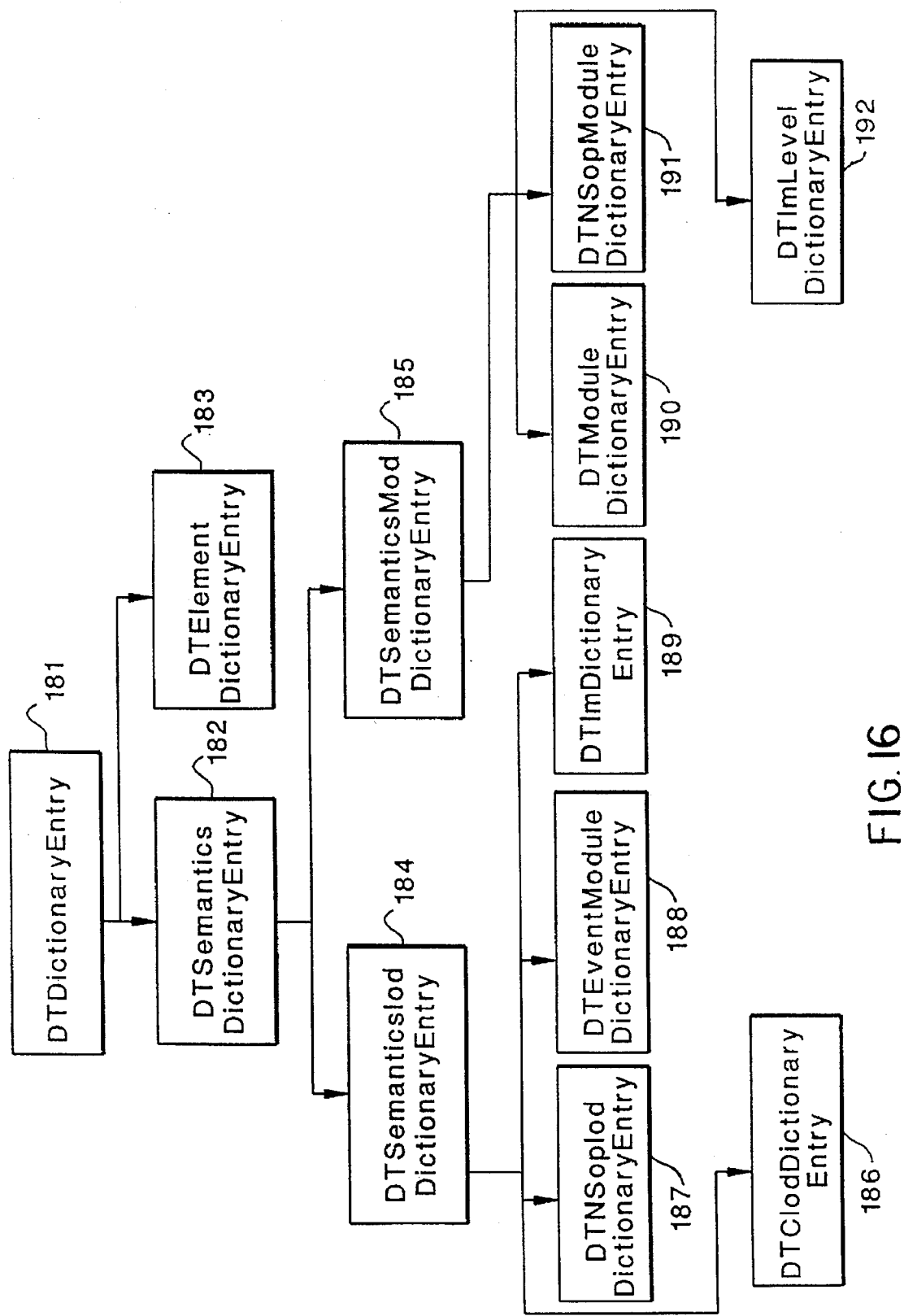
FIG. 16 is an illustration showing preferred inheritance relationships for DTDictionaryEntry in a preferred embodiment.

Turning now to FIG. 16, DTDictionaryEntry 181 provides an abstract class of items that are contained in a list by the DTDictionary class. This class identifies the name of a dictionary entry. It also points to a list of DTItemEntryDescription objects, which describe the items that are in a dictionary entry. DTSemanticsDictionaryEntry 182 provides an abstract class of items that are contained in a list by the DTSemanticsDictionary class. This class identifies the name of a semantics dictionary entry. It also points to a list of DTSemItemEntryDescription objects, which describe the items that are in this semantics dictionary entry. DTSemanticsIodDictionaryEntry 184 provides an abstract class of items that are contained in a list by the DTSemantics IodDictionary class. This class identifies the name of a Semantics IOD dictionary entry. It also points to a list of DTSemItemEntryDescription objects, which describe the items that are in this dictionary entry. DTCIodDictionaryEntry 186 provides a class of items that are contained in a list by a CompositeIodDictionary object. This object identifies the name of Composite IOD and points to a list of DTModuleIodDescription objects, which describe the modules that are in this composite IOD. DTNormalizedSopIodDicEntry 187 provides a class of items that are contained in a list by the DTNormalizedSopIodDictionary object. This object identifies the name of a normalized SOP IOD. It also points to a DTEventModuleSopDescription object and a list of DTNonEventModuleSopDescription objects, which describes each DIMSE service related IOD subset of definitions that are in a normalized SOP IOD.

DTEventModuleDictionaryEntry 188 provides a class of items that are contained in a list by the EventModuleDictionary object. The object identifies the name of a normalized event SOP IOD module. It also points to a list of DTEventTypeEventDescription objects, which describe each element in a normalized SOP IOD module. DTImDictionaryEntry 189 provides a class of items that are contained in a list by the DTImDictionary object. This object identifies the name of an IM. It also points to a list of DTKeyImDescription objects, which describe the keys that are in this IM.

DTSemanticsModDictionaryEntry 185 provides an abstract class of items that are contained in a list by the DTSemanticsModDictionary class. This class identifies the name of a semantics module dictionary entry. It also points to a list of DTSynItemEntryDescription objects, which describe the items that are in this dictionary entry. DTModuleDictionaryEntry 190 provides a class, a list of instances of which makes up the content of a single instance of DTModuleDictionary. This object identifies the name of a module and contains a list of pointers to DTElementModuleDescription objects, which describe the elements used in this module.

DTSopModuleDictionaryEntry 191 provides a class of items that are contained in a list by the DTSopModuleDictionary object. This object identifies the name of a SOP module. It also points to a list of DTElementSopDescription objects, which describes the elements that are in this dictionary entry. DTImLevelDictionaryEntry 192 provides a class of items that are contained in a list by the ImLevelDictionary object. This object identifies the name of an IM level. It also points to a list of DTKeyImLevelDescription objects, which describe the keys that are in an IM Level. DTElementDictionaryEntry 183 provides a class, a list of instances which makes up the content of the single instance of DTElementDictionary.

Figure 17:
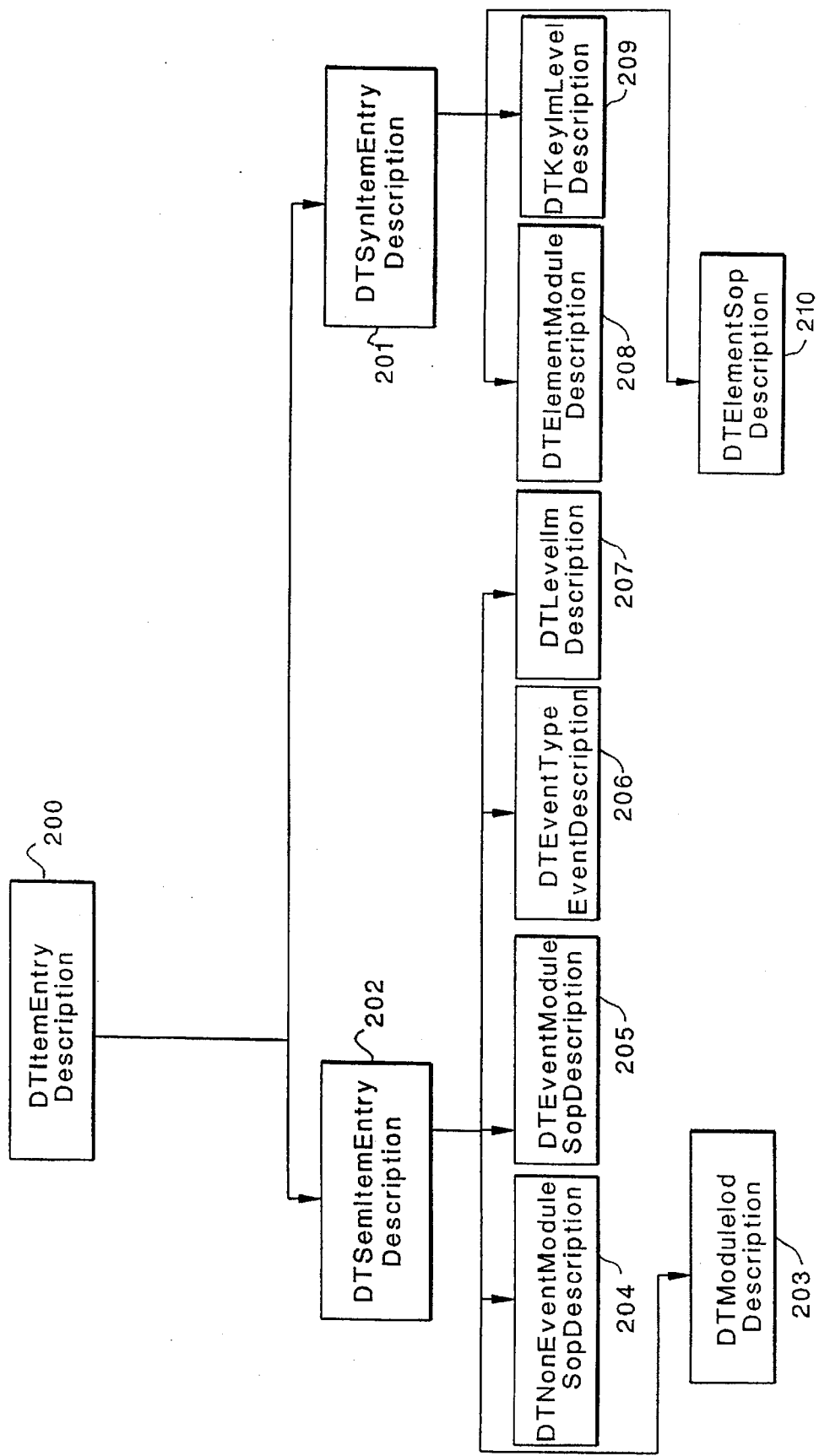
FIG. 17 is an illustration showing the inheritance relationships for DTItemEntryDescription in a preferred embodiment.

Turning now to FIG. 17, DTItemEntryDescription 200 provides an abstract class to describe an item that is part of a semantics dictionary entry. DTModuleIodDescription 203 provides a description of a module that is part of a Composite IOD, that is a DTCompositeIodDictionaryEntry owns a list of DTModuleIodDescription objects, that list describes the modules that are part of this Composite IOD. DTNonEventModuleSopDescription 204 provides a description of a non-event module that is part of a normalized SOP IOD. DTEventModuleSopDescription 205 provides a description of an event module SOP that is part of a normalized SOP IOD. DTEventTypeEventDescription 206 provides a description of an Event Type that is part of an event.

DTLevelImDescription 207 provides a description of a level that is part of an IM.

DTSynItemEntryDescription 201 provides an abstract class to describe an item that is part of a semantics module dictionary entry. DTElementModuleDescription 208 provides a semantic description of an element that is part of a module. It is a subclass of DTSynItemEntryDescription 201 from which it inherits data members and methods. DTSynItemEntryDescription 201 provides a description of an element that is part of a normalized SOP. DTElementSopDescription 210 provides a description of an element that is part of a normalized SOP. DTKeyImLevelDescription 209 provides a semantic description of a query key element that is part of an IM level.

Figure 18:
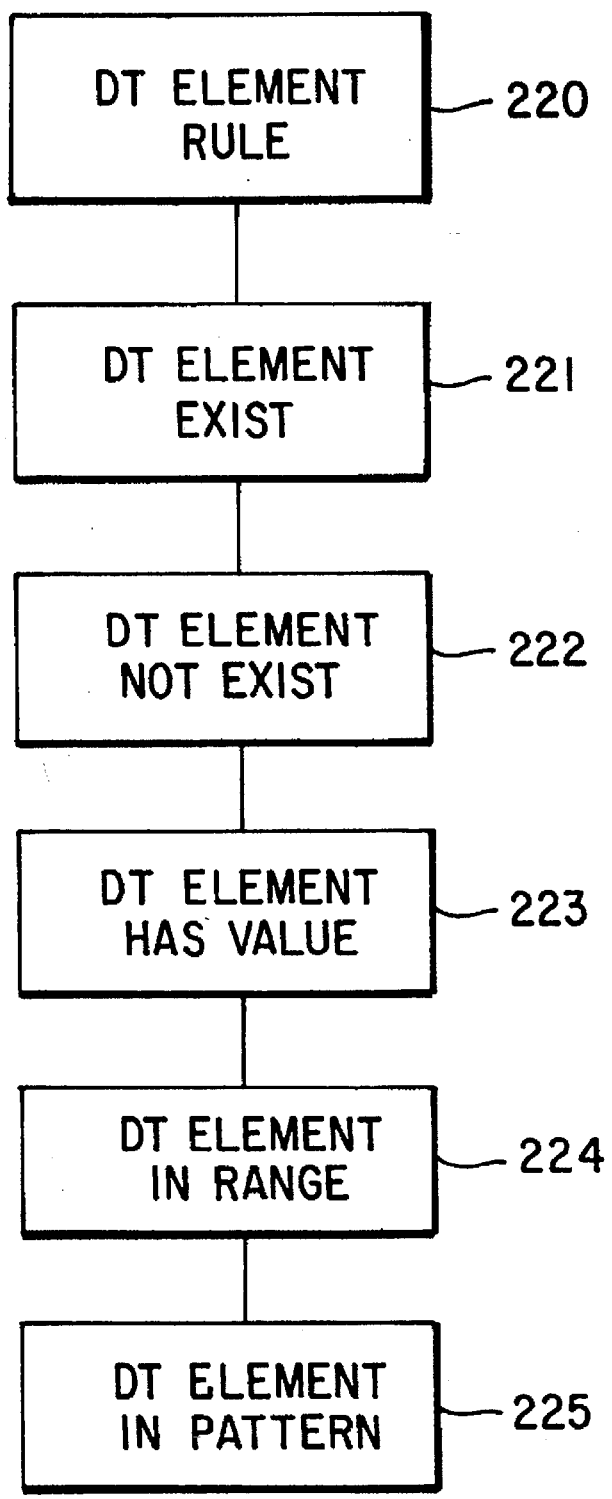
FIG. 18 is an illustration showing the inheritance relationships for DTElementRule in a preferred embodiment.

Turning now to FIG. 18, DTElement Rule 220 provides a general description of an element requirement condition role. There are a plurality of subclasses of this abstract class, one for each type of rule pattern defined. DTElementExist 221 provides a description of a specific rule type of element requirement condition. The pattern is "Element X exists."

DTElementNotExist 222 provides a description of a specific rule type of element requirement condition. The pattern is: "Element X does not exist." DTElementHasValue 223 provides a description of a specific rule type of element requirement condition. The pattern is: "Element X Has Value Y." DTElementInRange 224 provides a description of a specific rule type of element requirement condition. The pattern is: "Element X value is greater than Y1 and less than or equal to Y2." DTElementInPattern 225 provides a description of a specific rule type of element requirement condition. The pattern is: "Element X value matches pattern Y . . . specifically Element X value is in (Y1IY2IY3I . . . IYN)."

The invention is defined by the following claims.

What is claimed is:

1. A method for validating a DICOM message comprising the steps of:
   (a) transforming a physical image on radiological film into a digital image;
   (b) storing the digital image in computer memory;
   (c) encapuslating the digital image in a DICOM message in computer memory;
   (d) accessing a dictionary in computer memory to obtain a list of elements and modules comprising the DICOM message;
   (e) building a validation list in computer memory for the DICOM message;
   (f) accessing a dictionary in computer memory to obtain a set of rules for validating the elements and modules comprising the DICOM message;
   (g) accessing a dictionary in computer memory to obtain a set of warnings associated with the rules for validating the elements and modules comprising the DICOM message;
   (h) comparing the rules to the elements and modules comprising the DICOM message;
   (I) generating a warning when an element or module violates a
   (j) storing the warning in the validation list in computer memory; and
   (l) examining the validation list to determine whether the DICOM message is semanticly conforming with a DICOM standard.

2. The method of claim 1 wherein step (d) of claim 1 further comprises the step of:
   accessing a dictionary in computer memory to obtain names for the elements.

3. The method of claim 2 further comprising the step of:
   accessing a dictionary in computer memory to obtain names for the modules.

4. The method of claim 3 further comprising the step of:
   accessing a dictionary in computer memory to obtain tags for the modules.

5. The method of claim 4 further comprising the step of:
   accessing a dictionary in computer memory to obtain tags for the elements.

6. The method of claim 4 further comprising the step of:
   accessing a dictionary in computer memory to obtain descriptions for the modules.

7. The method of claim 4 further comprising the step of:
   accessing a dictionary in computer memory to obtain descriptions for the elements.

8. The method of claim 4 further comprising the step of:
   accessing a dictionary in computer memory to obtain values for the elements.

9. The method of claim 4 further comprising the step of:
   accessing a dictionary in computer memory to obtain conditions for the modules.

10. An appartus for validating a DICOM message comprising:
    (a) a digital computer having a processor and computer memory containing a DICOM message;
    (b) a dictionary class of objects stored in computer memory describing the DICOM message;
    (c) an entry description class of objects derived from the dictionary class and stored in computer memory;
    (d) an item description class of objects derived from the dictionary class and stored in computer memory;
    (e) a module description class of objects derived from the dictionary class and stored in computer memory;
    (f) a semantic role description class of objects derived from the dictionary class and stored in computer memory;
    (g) a semantic warning description class of objects derived from the dictionary class and stored in computer memory; and
    (h) a semantic warning list stored in computer memory.

11. The apparatus of claim 10 wherein the entry description class of objects comprises an entry description for modules in the DICOM message.

12. The apparatus of claim 11 wherein the entry description class of objects further comprises an entry description for elements in the DICOM message.

13. The apparatus of claim 12 wherein the item description class of objects comprises an item description for modules in the DICOM message.

14. The apparatus of claim 13 wherein the item description class of objects further comprises an item description for elements in the DICOM message.

15. The apparatus of claim 14 wherein the module description class of objects comprises an entry description for modules in the DICOM message.

16. The apparatus of claim 15 wherein the entry description class of objects further comprises an entry description for elements in the DICOM message.

17. The apparatus of claim 16 wherein the entry description class of objects comprises an entry description for modules in the DICOM message.

18. The apparatus of claim 17 wherein the semantic rule description class of objects further comprises semantic rules for elements in the DICOM message.

19. The apparatus of claim 18 wherein the semantic rule description class of objects further comprises a semantic rule description for modules in the DICOM message.

20. The apparatus of claim 19 wherein the semantic warning description class of objects further comprises semantic warning descriptions for modules and elements in the DICOM message.

* * * * *